(12) United States Patent
Babich et al.

(10) Patent No.: US 9,878,980 B2
(45) Date of Patent: Jan. 30, 2018

(54) HETERODIMERS OF GLUTAMIC ACID

(71) Applicant: Molecular Insight Pharmaceuticals, Inc., Cambridge, MA (US)

(72) Inventors: John W. Babich, Cambridge, MA (US); Craig N. Zimmerman, Cambridge, MA (US); Kevin P. Maresca, Cambridge, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/337,867

(22) Filed: Oct. 28, 2016

(65) Prior Publication Data

US 2017/0044098 A1    Feb. 16, 2017

Related U.S. Application Data

(60) Continuation of application No. 15/068,841, filed on Mar. 14, 2016, which is a division of application No. 13/271,549, filed on Oct. 12, 2011, now Pat. No. 9,309,193, which is a division of application No. 11/936,659, filed on Nov. 7, 2007, now abandoned.

(60) Provisional application No. 60/857,490, filed on Nov. 8, 2006, provisional application No. 60/878,678, filed on Jan. 5, 2007.

(51) Int. Cl.

| A61K 51/04 | (2006.01) |
|---|---|
| A61K 49/00 | (2006.01) |
| C07C 275/16 | (2006.01) |
| C07B 59/00 | (2006.01) |
| C07C 275/24 | (2006.01) |
| C07C 275/30 | (2006.01) |
| C07C 311/19 | (2006.01) |
| C07D 213/38 | (2006.01) |
| A61K 39/385 | (2006.01) |

(52) U.S. Cl.
CPC .......... *C07C 275/16* (2013.01); *A61K 39/385* (2013.01); *C07B 59/001* (2013.01); *C07C 275/24* (2013.01); *C07C 275/30* (2013.01); *C07C 311/19* (2013.01); *C07D 213/38* (2013.01)

(58) Field of Classification Search
None
See application file for complete search history.

(56) References Cited

U.S. PATENT DOCUMENTS

| 3,527,789 | A | 9/1970 | Payne |
|---|---|---|---|
| 4,885,136 | A | 12/1989 | Katayama et al. |
| 4,888,136 | A | 12/1989 | Chellapa et al. |
| 5,442,088 | A | 8/1995 | Hoffmann |
| 5,672,592 | A | 9/1997 | Jackson et al. |
| 5,739,123 | A | 4/1998 | Norcini et al. |
| 5,795,877 | A | 8/1998 | Jackson et al. |
| 5,824,662 | A | 10/1998 | Slusher et al. |
| 5,880,112 | A | 3/1999 | Jackson et al. |
| 6,071,965 | A | 6/2000 | Jackson et al. |
| 6,479,470 | B1 | 11/2002 | Kozikowski et al. |
| 6,528,499 | B1 | 3/2003 | Kozikowski et al. |

(Continued)

FOREIGN PATENT DOCUMENTS

| EP | 3878463 | 11/1998 |
|---|---|---|
| WO | 1997048399 | 12/1997 |
| WO | 1997048400 | 12/1997 |
| WO | 1997048409 | 12/1997 |
| WO | 1998013046 | 4/1998 |
| WO | 1998045256 | 10/1998 |
| WO | 1998045257 | 10/1998 |
| WO | 1999033847 | 7/1999 |
| WO | 2000064911 | 11/2000 |
| WO | 2001001974 | 1/2001 |
| WO | 200222627 | 3/2002 |
| WO | 2003060523 | 7/2003 |
| WO | 2006093991 | 9/2006 |
| WO | 2008058192 | 5/2008 |

OTHER PUBLICATIONS

Office Action cited in U.S. Appl. No. 12/029,367 dated Oct. 19, 2010.

(Continued)

*Primary Examiner* — Marcos Sznaidman
*Assistant Examiner* — Rayna B Rodriguez
(74) *Attorney, Agent, or Firm* — K&L Gates LLP

(57) ABSTRACT

Compounds of Formula (Ia)

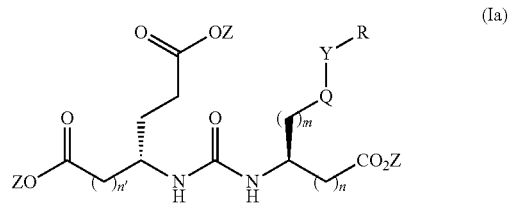

wherein R is a $C_6$-$C_{12}$ substituted or unsubstituted aryl, a $C_6$-$C_{12}$ substituted or unsubstituted heteroaryl, a $C_1$-$C_6$ substituted or unsubstituted alkyl or —NR'R',
Q is C(O), O, NR', S, S(O)$_2$, C(O)$_2$(CH2)p
Y is C(O), O, NR', S, S(O)$_2$, C(O)$_2$(CH2)p
Z is H or $C_1$-$C_4$ alkyl,
R' is H, C(O), S(O)$_2$, C(O)$_2$, a $C_6$-$C_{12}$ substituted or unsubstituted aryl, a $C_6$-$C_{12}$ substituted or unsubstituted heteroaryl or a $C_1$-$C_6$ substituted or unsubstituted alkyl, when substituted, aryl, heteroaryl and alkyl are substituted with halogen, $C_6$-$C_{12}$ heteroaryl, —NR'R' or COOZ, which have diagnostic and therapeutic properties, such as the treatment and management of prostate cancer and other diseases related to NAALADase inhibition, Radiolabels can be incorporated into the structure through a variety of prosthetic groups attached at the X amino acid side chain via a carbon or hetero atom linkage.

3 Claims, 20 Drawing Sheets

(56) References Cited

U.S. PATENT DOCUMENTS

| | | |
|---|---|---|
| 7,381,745 B2 | 6/2008 | Kozikowski et al. |
| 8,487,129 B2 | 7/2013 | Babich et al. |
| 9,309,193 B2 | 4/2016 | Babich et al. |
| 2004/0002478 A1 | 1/2004 | Kozikowski et al. |
| 2004/0054190 A1 | 3/2004 | Pomper et al. |
| 2006/0155021 A1 | 7/2006 | Lenges et al. |
| 2006/0155146 A1 | 7/2006 | Lenges et al. |
| 2006/0198785 A1 | 9/2006 | Santos et al. |
| 2008/0176821 A1 | 7/2008 | Kozikowski et al. |
| 2008/0193381 A1 | 8/2008 | Babich et al. |
| 2011/0008253 A1 | 1/2011 | Babich et al. |
| 2012/0208988 A1 | 8/2012 | Babich et al. |
| 2012/0269726 A1 | 10/2012 | Babich et al. |

OTHER PUBLICATIONS

Carter et al.,"Prostate-Specific Membrane Antigen Is a Hydrolase With Substrate and Pharmacologic Characteristics of a Neuropeptidase," Proc. Nat. Acad. Sci. USA, 93:749-753 (1996).

Gasparini et al., "(R.S)-4-Phosphononphenyglince, a Potent and Selective Group III Metabotropic Glutamate Receptor Agonist, Is Anticonvulsive and Neuroprotective in Vivo," J. Pharm. Exper. Ther., 289(3):1678-1687 (1999).

Izdebski et al., "Synthesis of N,N'-Carbonyl-Bis Amino Acids and N,N'-Carbonyl-Bis-Peptides," Polish J. Chem., 71(8):1066-1074 (1997).

Jackson et al., "Design, Synthesis, and Biological Activity of a Potent Inhibitor of the Neuropeptidase Nacetylated or Linked Acidic Dipeptidase," J. Med. Chem., 39(2):619-622 (1996).

Kozikowski et al., "Design of Remarkably Simple, Yet Potent Urea-Based Inhibitors of Glutamate Carboxypeptidase II (Naaladase)," J. Med. Chem. 44(3):298-301 (2001).

Lewis, Hawley's Condensed Chemical Dictionary, 12 Ed., Van Nostrand Reinhold Co., New York, NY, 9, 420, 421 and 881 (1993).

Nam et al., "Dual Function Glutamate-Related Ligands: Discovery of a Novel, Potent Inhibitor of Glutamate Carboxypeptidase II Possessing MGLUR3 Agonist Activity," J. Med. Chern., 43(5):772-774 (2000).

Slusher, et al., "Rat Brain N-Acetylated or Linked Acidic Dipeptidase Activit," J. Biolog. Chem., 265(34):21297-321301 (1990).

Slusher, et al., "Immunocytochemical Localization of the N-Acety-Aspartyl-Glutamate (NAAG) Hydrolyzing Enzyme N-Acetylated or Linked Acidic Dipeptidase (Naaladase)," J. Compar. Neurol., 315(2):217-229 (1992).

6001 Chemical Abstracts, Columbus Ohio, US, 101(27). XP 002196919 (1984).

International Search Report for International Application No. PCT/US2000/011262 dated Mar. 12, 2000 (4 Pages).

International Search Report for International Application No. PCT/US2007/083934 dated Mar. 13, 2008 (1 Page).

European Search Report for International Application No. PCT/US2007/083934 dated May 13, 2012 (6 Pages).

Kozikowski et al., "Synthesis of Urea-Based Inhibitors as Active Site Probes of Glutamate Carboxypeptidase II: Efficacy as Analgesic Agents," J. Med. Chem., 47:1729-1738 (2004).

Foss et al., "Radiolabeled Small-Molecule Ligands for Prostate-Specific Membrane Antigen: In Vivo Imaging in Experimental Models of Prostate Cancer," Clin. Cancer Res., 11(11):4022-4028 (2005).

Silver, et al. "Prostate-specific membrane antigen expression in normal and malignant human tissues" Clin. Cancer Res., [1997], vol. 3, pp. 81-85.

Cherry "In vivo molecular and genomic imaging: new challenges for imaging physics" Phys Med Biol. [2004], vol. 49, pp. R13-R48.

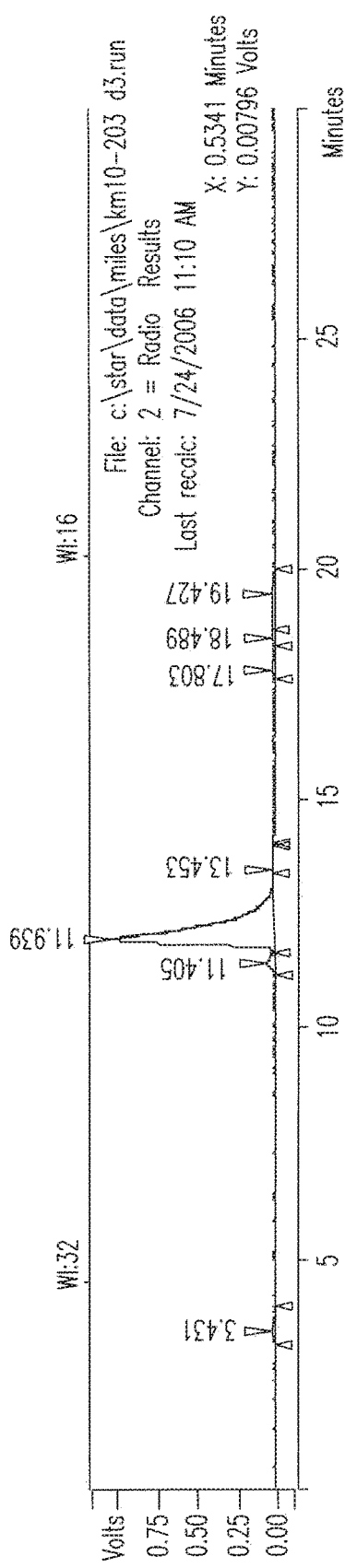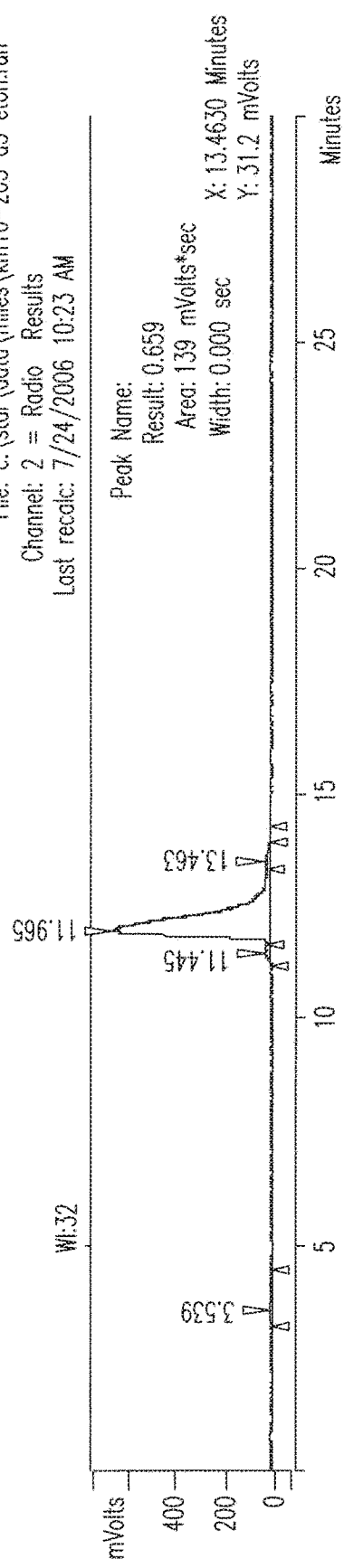
FIG.4A
FIG.4B

| Compound | $K_i$ (nM) |
|---|---|
| PMPA | 2.2 |
| DCT | 1.8 |
| MIP-1072 | 6.1 |
| MIP-1095 | 0.2 |
| MIP-1097 | 0.7 |

$$K_i = \frac{IC_{50}}{1 + \frac{[S]}{K_m}}$$

[S] = 1000 nM    $K_m$ = 200 nM*

| | $IC_{50}$ (nM) |
|---|---|
| MIP-1035 | 30 |
| MIP-1089 | 361 |
| MIP-1072 | 22 |
| MIP-1094 | 43 |
| MIP-1090 | 1380 |
| MIP-1106 | 2960 |

HETERODIMERS OF GLUTAMIC ACID

CROSS-REFERENCE TO RELATED APPLICATIONS

This application is a continuation of U.S. patent application Ser. No. 15/068,841 filed on Mar. 14, 2016; which is a divisional of U.S. patent application Ser. No. 13/271,549, now U.S. Pat. 9,309,193, filed on Oct. 12, 2011; which is a first divisional of parent application, U.S. patent application Ser. No. 11/936,659filed on Nov. 7, 2007, now abandoned; which claims priority to and the benefit of U.S. provisional patent application No. 60/857,490 filed on Nov. 8, 2006 and U.S. provisional patent application No. 60/878,678 filed on Jan. 5, 2007, both now expired; the disclosures of each of the foregoing are incorporated herein by reference in their entireties.

BACKGROUND OF THE INVENTION

At least 1 million men suffer from prostate cancer and its estimated that the disease will strike one in six U.S. men between the ages of 60 and 80. There are more than 300,000 new cases of prostate cancer diagnosed each year. Prostate cancer will affect one in six man in the United Stares, and the mortality from the disease is second only to lung cancer. An estimated $2 billion in currently spent worldwide on surgical, radiation, drug therapy and minimally invasive treatments, $1 billion of the spending in the U.S. There is presently no effective therapy for relapsing, metastatic, androgen-independent prostate cancer. New agents that will enable rapid visualization of prostate cancer and specific targeting to allow radiotherapy present are needed.

N-acetylated alpha-linked acidic dipeptidase (NAALADase), also known as glutamate carboxypeptidase II (GC-PII) is a neuropeptidase which cleaves N-acetylaspartyl-glutamate (NAAG) into N-acetylaspartate and glutamate in the nervous system, see below, depicting hydrolytic cleavage of NAAG by NAALDase through the tetrahedral intermediate. The enzyme is a type II protein of the co-catalytic class of metallupeptidases, containing two zinc atoms in the active site.

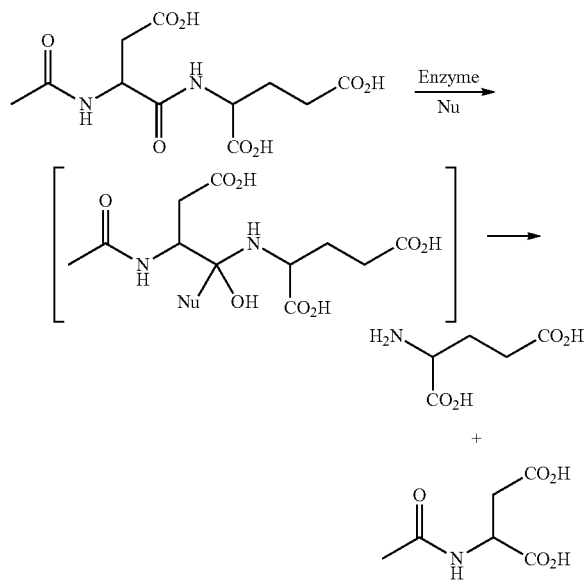

Independent of its characterization in the nervous system, one form of NAALADase was shown to be expressed at high levels in human prostatic adenocarcinomas and was designated the prostate-specific membrane antigen (PSMA). The NAALADase/PSMA gene is known to produce multiple mRNA splice forms and based on previous immuno-histochemical evidence, it has been assumed that the human brain and prostate expressed different isoforms of the enzyme.

Human prostate-specific membrane antigen (PSMA), also known as folate hydrolase 1 (FOLH1), is a trans-membrane, 750 amino acid type II glycoprotein which is primarily expressed in normal human prostate epithelium but is upregulated in prostate cancer, including metastiatic disease. PSMA is a unique exopeptidase with reactivity toward poly-gamma-glutamated folates, capable of sequentially removing the poly-gamma-glutamyl termini. Since PSMA is expressed virtually all prostate cancers and its expression is further increased in poorly differentiated, metastiatic and hormone-refractory carcinomas, it is a very attractive target for prostate imaging and therapy. Developing ligands that interest with PSMA and carry appropriate radionuclides may provide a promising and novel targeting option for the detection, treatment and management of prostate cancer.

The radio-immunoconjugate form of the anti-PSMA monoclonal antibody (mAb) 7E11, known as the PROSTASCINT scan, is currently being used to diagnose prostate cancer metastasis and recurrence. Early promising results from various Phase I and II trials have utilized PSMA as a therapeutic target. PROSTASCINT targets the intracellular domain of PSMA and is thought to bind mostly necrotic portions of prostate tumor.[14] More recently, monoclonal antiobodies have been developed that bind to the extracellular domain of PSMA and have been radiolabeled and shown to accumulate in PSMA-positive prostate tumor models in animals.

While monoclonal antibodies hold promise for tumor detection and therapy, there have been limited clinical successes outside of lymphoma because of their low permeability in solid tumors. Low molecular weight mimetics, with higher permeability in solid tumors will have a definite advantage in obtaining high percent per gram and a high percentage of specific binding.

SUMMARY OF THE INVENTION

One aspect of the present invention relates to compounds of Formula (I)

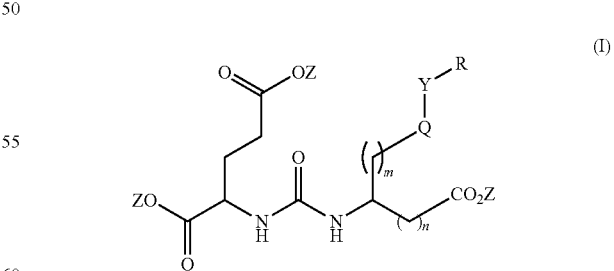

wherein R is a $C_6$-$C_{12}$ substituted or unsubstituted aryl, a $C_6$-$C_{12}$ substituted or unsubstituted heteroaryl, a $C_1$-$C_6$ substituted or unsubstituted alkyl or —NR'R', Q is C(O), O, NR', S, $S(O)_2$, $C(O)_2(CH2)p$ Y is C(O), O, NR'S, $S(O)_2$, $C(O)_2(CH2)p$ Z is H or $C_1$-$C_4$ alkyl, m is 0, 1, 2, 3, 4 or 5
n is 0, 1, 2, 3, 4, 5 or 6
p is 0, 1, 2, 3, 4, 5 or 6
R' is H, C(O), S(O)$_2$, C(O)$_2$, a C$_6$-C$_{12}$ substituted or unsubstituted aryl, a C$_6$-C$_{12}$ substituted or unsubstituted heteroaryl or a C$_1$-C$_6$ substituted or unsubstituted alkyl, when substituted, aryl, heteroaryl and alkyl are substituted with halogen, C$_6$-C$_{12}$ heteroaryl, —NR'R' or COOZ,
further wherein
(i) at least one of R or R' is a C$_6$-C$_{12}$ aryl or C$_6$-C$_{12}$ heteroaryl substituted with a halogen or
(ii) at least one of R or R' is a C$_6$-C$_{12}$ heteroaryl or a pharmaceutically acceptable salt of the compound of Formula (I).

Another aspect of the present invention relates to compounds of Formula (Ia)

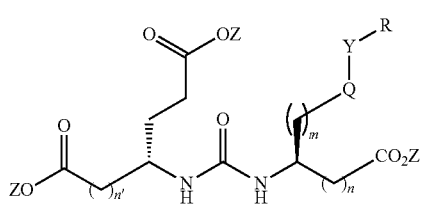

(Ia)

wherein R is a C$_6$-C$_{12}$ substituted or unsubstituted aryl, a C$_6$-C$_{12}$ substituted or unsubstituted heteroaryl, a C$_1$-C$_6$ substituted or unsubstituted alkyl or —NR'R',
Q is C(O), O, NR', S, S(O)$_2$, C(O)$_2$(CH2)p
Y is C(O), O, NR'S, S(O)$_2$, C(O)$_2$(CH2)p
Z is H or C$_1$C$_4$ alkyl,
m is 0, 1, 2, 3, 4 or 5
n 0, 1, 2, 3, 4, 5 or 6
n' 0, 1, 2, 3, 4, 5 or 6
p is 0, 1, 2, 3, 4, 5 or 6
R' is H, C(O), S(O)$_2$, C(O)$_2$, a C$_6$-C$_{12}$ substituted or unsubstituted aryl, a C$_6$-C$_{12}$ substituted or unsubstituted heteroaryl or a C$_1$-C$_6$ substituted or unsubstituted alkyl, when substituted, aryl, heteroaryl and alkyl are substituted with halogen, C$_6$-C$_{12}$ heteroaryl, —NR'R' or COOZ,
further wherein
(i) at least one of R or R' is a C$_6$-C$_{12}$ aryl or C$_6$-C$_{12}$ heteroaryl substituted with a halogen or
(ii) at least one of R or R' is a C$_6$-C$_{12}$ heteroaryl or a pharmaceutically acceptable salt of the compound of Formula (I).

In a preferred embodiment of the compounds of Formulas (I), (Ia), (II) or (IIa) n is 0 or 1 and n' is 0 or 1.

The present invention also relates to glutamate-urea-lysine PSMA-binding moieties and their use in diagnostic and therapeutic treatment. In one embodiment, the urea-based analogues described here are glutamate-urea-α or β-amino acid heterodimer coupled through the α-NH$_2$ or β-NH$_2$ groups. Radiolabels can be incorporated into the structure through a variety of prosthetic groups attached at the X amino acid side chain via a carbon or hetero atom linkage. The compounds of the present invention can find use as targeting agents and diagnostic and therapeutic agents for the treatment and management of prostate cancer and other diseases related to NAALADase inhibition.

Suitable chemical moieties, definitions of chemical moieties, excipients and methods and modes of administration can be found is US Published Application Nos. 2004/0054190 and 2004/0002478 and International Application Nos. WO 02/22627 and WO 03/060523, which are incorporated by reference in their entirety.

BRIEF DESCRIPTION OF THE DRAWINGS

FIG. 4A-4D are radio-HPLC chromatograms of I-131 MIP 1072 purified; at 3 days in A) DMSO. B) 3% genstisate-6% Ascorbate/Ascorbic acid, C) PBS, pH=7.2, D) 10% Ethanol in Saline at 37° C. As shown above, the I-131-1072 (peak 12 minutes) remained stable throughout the experiments.

DETAILED DESCRIPTION OF THE INVENTION

Definitions

Figure 1A:
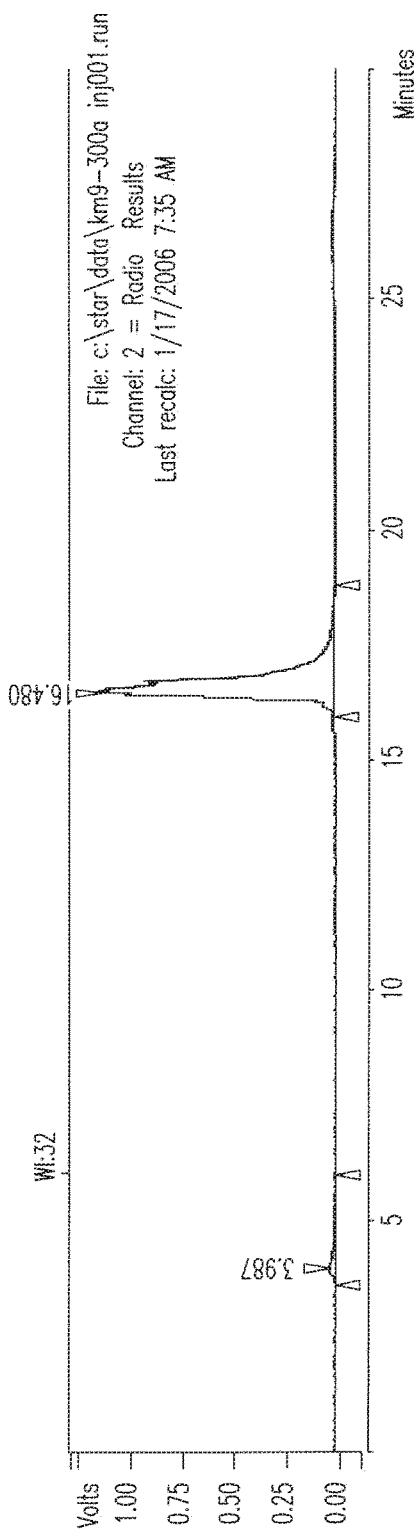
FIGS. 1A-1C are HPLC chromatograms respectively of the co-injection of the TC-99m-glu-urea-DpK (Tc-99m-MIP 1008), the rhenium analog, and rhenium diester complexes.
Figure 1B:
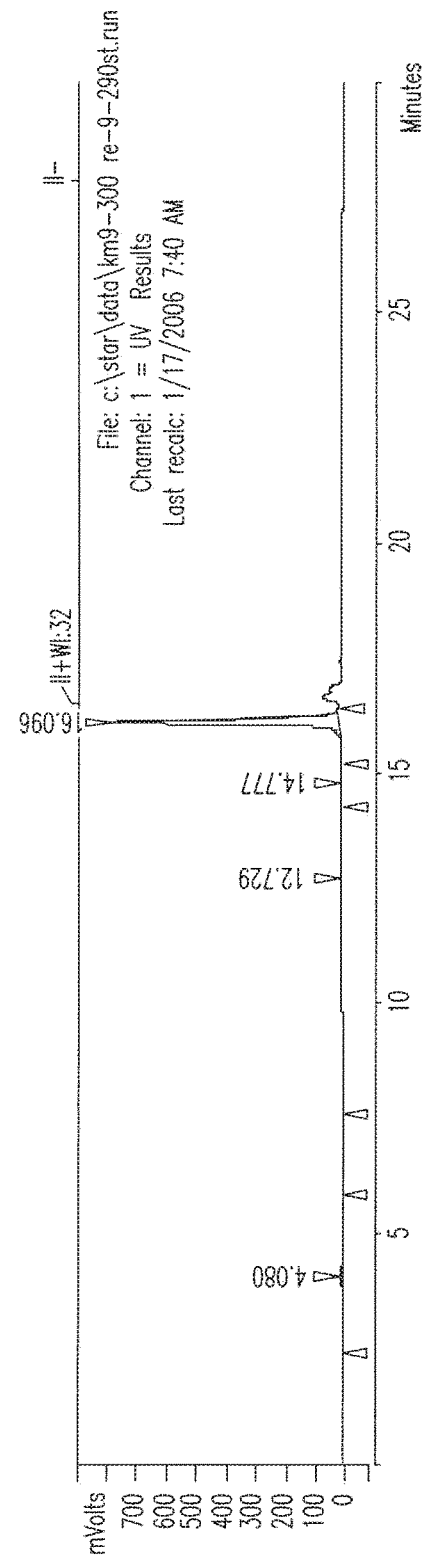
Figure 1C:
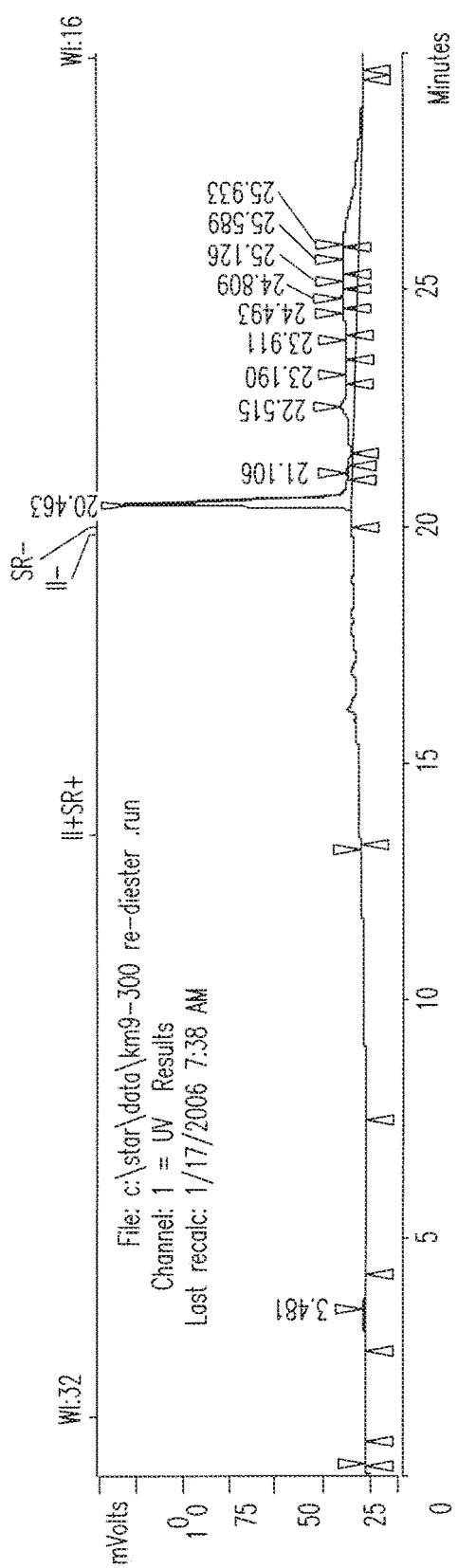
Figure 2A:
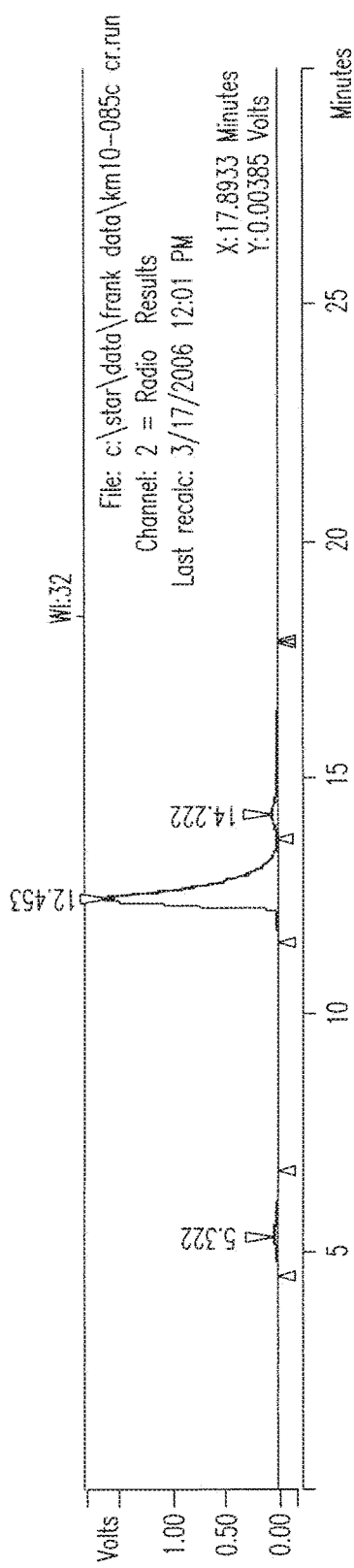
FIGS. 2A-2D show stability of the Tc-99m complex of Glu-urea-DpK (Tc-99m-MIP 1008) at 37° C. in respectively PBS pH 7.2, 0.1 M Cysteine in PBS, 0.1 M DTPA in PBS, and 5% mouse serum in PBS for 6 hours.
Figure 2B:
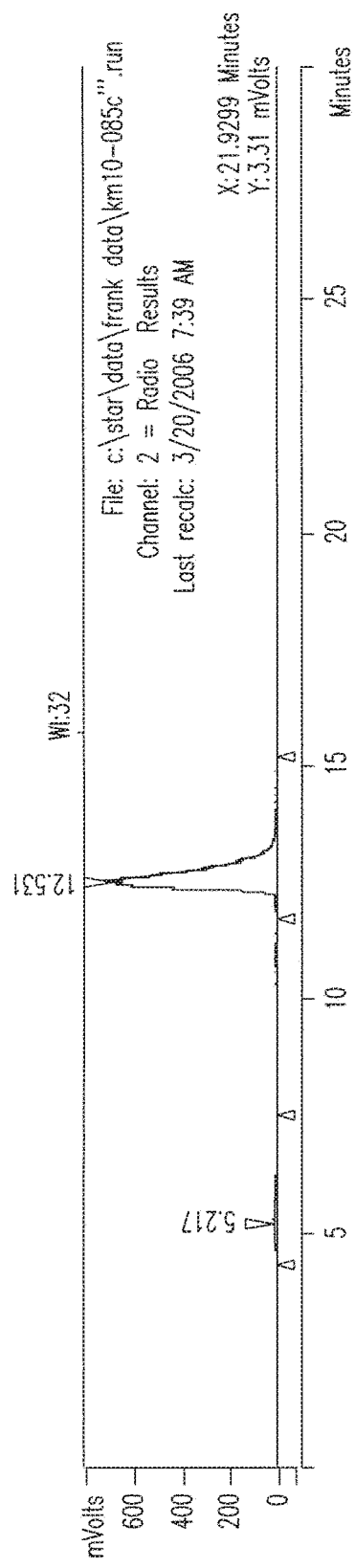
Figure 2C:
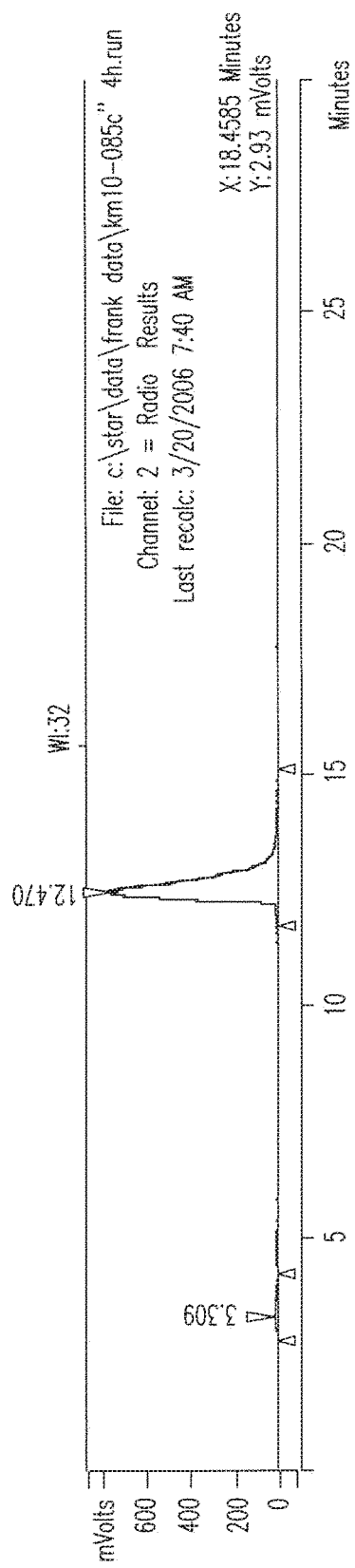
Figure 2D:
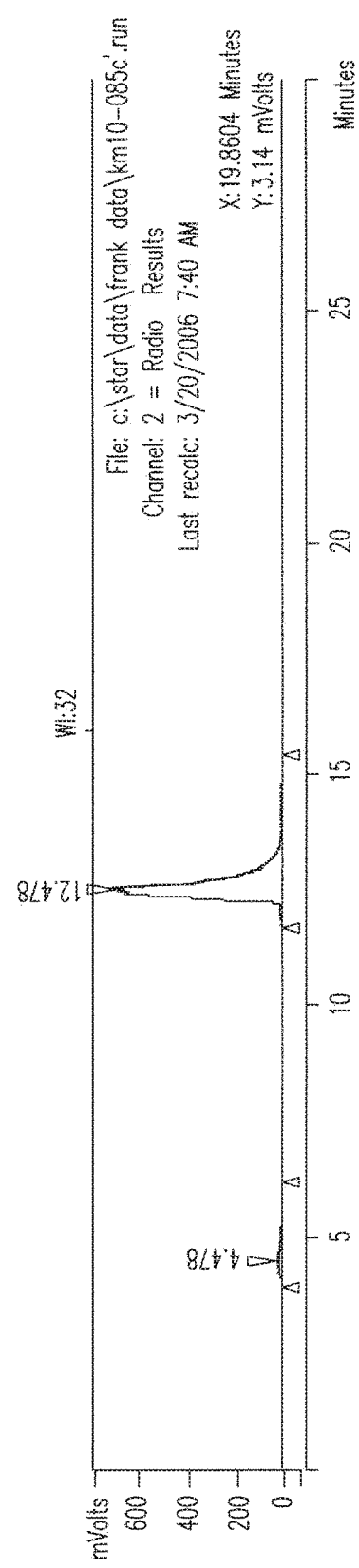

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, or alkoxy. When the alky group is an R' substituent, it is a lower alkyl of from 1 to 6 carbons, more preferably 1 to 4 carbons.

"Aryl" refers to an aromatic group which has a least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino. Examples of aryl groups include phenyl, napthyl and anthracyl groups. Phenyl and substituted phenyl groups are preferred.

"Heteroaryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

Synthesis

All reactions were carried out in dry glassware under an atmosphere of argon unless otherwise noted. Reactions were purified by column chromatography, under medium pressure using a Biotage SP4 or by preparative high pressure liquid chromatography.

$^1$H NMR was recorded on a Bruker 400 MHz instrument. Spectra are reported as ppm δ are referenced to the solvent resonances in CDCl$_3$, DMSO-d$_6$ or methanol-d$_4$. All solvents were purchased from Sigma-Aldrich. Reagents were purchased from Sigma Aldrich, Bachem, Akaal, Fisher, Alfa Aesar, Acros and Anaspec. The following abbreviations are used methylene chloride (DCM), ethyl acetate (EA), hexanes (Hex), dichloroethane (DCE), dimethyl formamide (DMF), trifluoroacetic acid (TFA), tetrahydrofuran (THF), carbonyldiimidazole (CDI), dimethylaminopyridine (DMAP), triethylamine (TEA), methyl trifluoromethanesulfonate (MeOTf), (S)-2-Amino-6-(bis-pyridin-2-ylmethylamino)-hexanoic acid (dpK), glutamic acid (Glu), diisopropylethylamine (DIEA), benzyloxycarbonyl (CBZ).

Synthesis of Intermediates

The following compounds were all prepared in overall yields ranging from 20-40% following the route depicted in Scheme 1. The first step, performed at 0° C. under inert conditions used the di-t-butyl ester of Glutamic acid with CDI in the presence of base to form the intermediate Glu-urea-imidazole derivative 2. This intermediate was activated with MeOTf under basic conditions to afford the methylated imidazole 3, which under inert conditions reacted readily with amines. The tert-butyl ester protecting groups were removed using 20% TFA in DCM for 1 to 4 hour at room temperature. Upon completion of the deprotection, the reactions were concentrated on a rotary evaporator or blown dry with nitrogen and purified on a silica column or recrystallized. The final products were tested in vitro and in vivo.

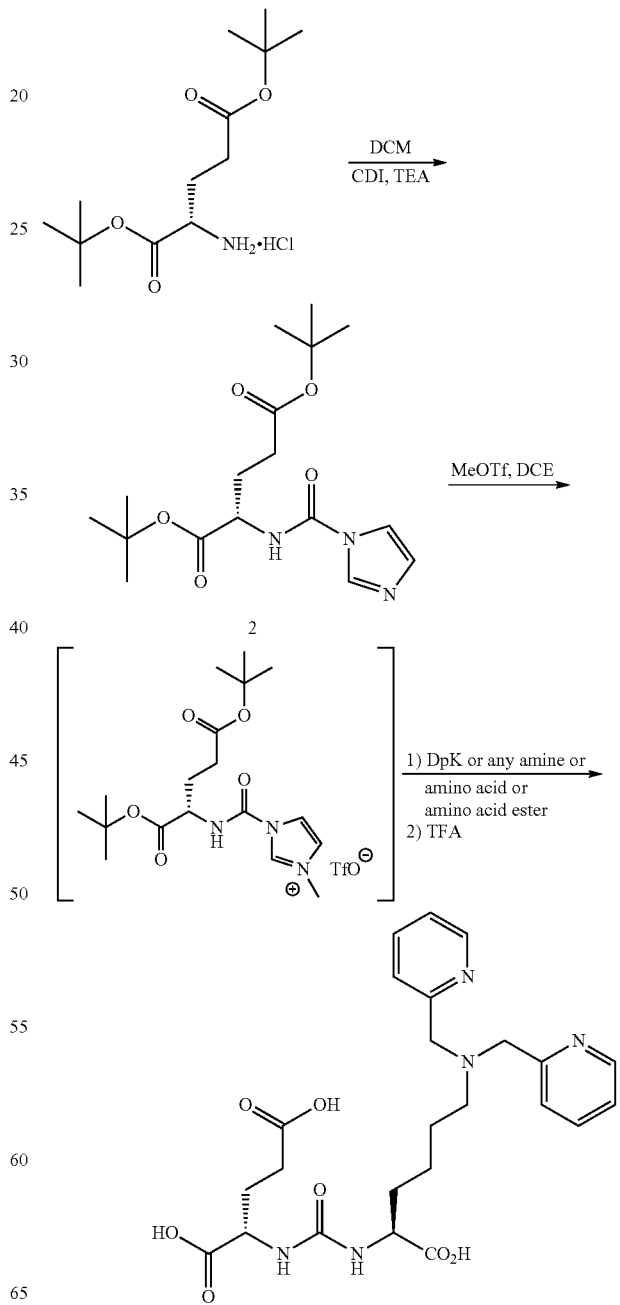

Scheme 1. General pathway for the synthesis of PSMA compounds.

L-(S)-2-[(Imidazole-1-carbonyl)-amino]-pentanedioic acid di-tert-butyl ester (2)

To a suspension of di-t-butyl glutamate hydrochloride (15.0 g, 51 mmol) in DCM (150 mL) cooled to 0° C. was added TEA (18 mL) and DMAP (250 mg). After stirring for 5 min. CDI (9.0 g, 56 mmol) was added and the reaction was stirred overnight with warming to room temperature. The reaction was diluted with DCM (150 mL) and washed with saturated sodium bicarbonate (60 mL), water (2×100 mL) and brine (100 mL). The organic layer was dried over sodium sulfate and concentrated to afford the crude product as s semi-solid, which slowly solidified upon standing. The crude material was triturated with hexane/ethyl acetate to afford a white solid which was filtered, washed with hexane (100 mL) and dried to afford the desired product (15.9 g, 45 mmol, 88%) as a white solid. $^1$H NMR (400 MHz, DMSO-d$_6$) δ7.63 (s, 1H), 7.00 (br, 2H), 6.31 (d,1H), 4.02 (m, 1H), 2.19 (m, 2H), 1.86 (m, 1H), 1.67 (m, 1H), 1.39 (s, 9H), 1.38 (s, 9H). ESMS m/z: 354 (M+H)$^+$.

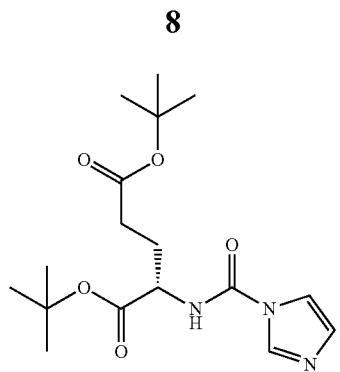

Alternatively, the analogs can be prepared via the isocyanate generated in situ using triphosgene. This approach can be accomplished by either activation of the glutamate residue and coupling with a lysine residue (route A) or by activating the lysine residue and coupling it with the glutamate (route B) as shown in scheme 2 below.

Scheme 2.

Route A

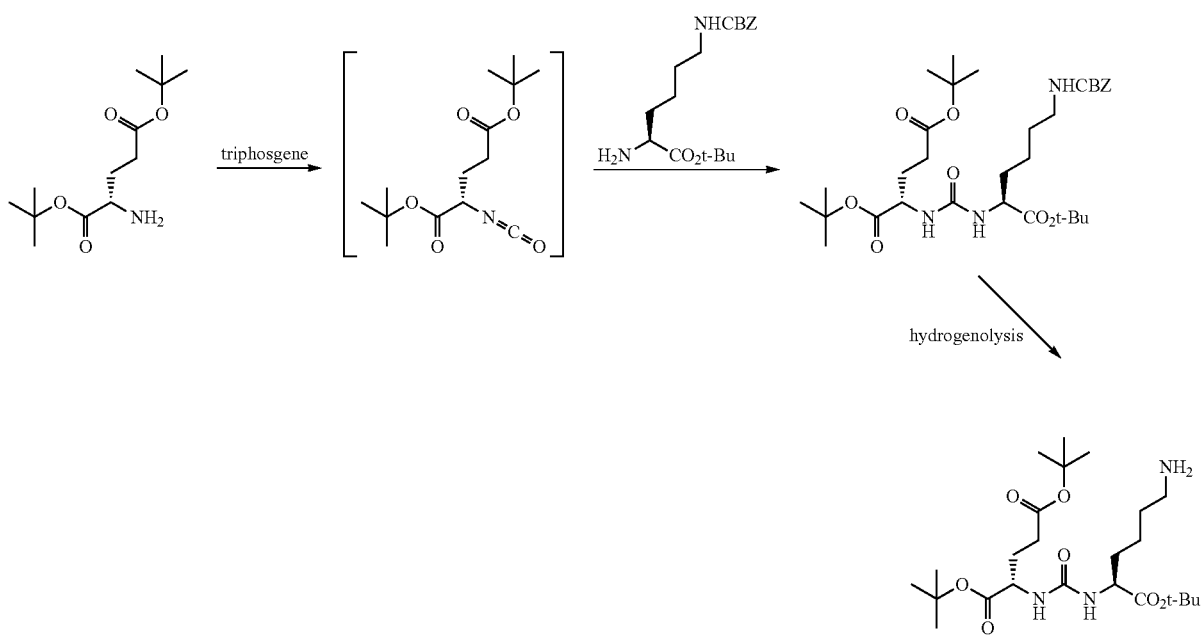

Route B

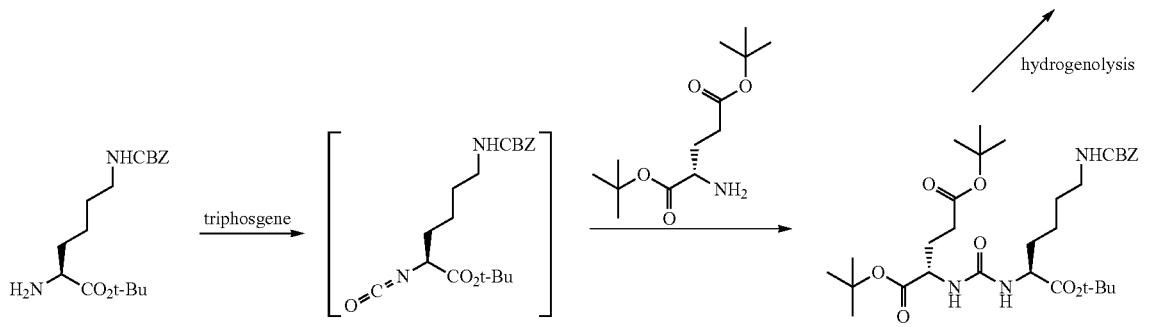

L-(S,S)-2-[3-(5-Benzyloxycarbonylamino-1-tert-butoxycarbonyl-pentyl-ureido)-pentanedioic acid di-tert-butyl ester (3)

Route A. In a round bottom flask 1.8 mL TEA (13.2 mmol) was combined with 1.8 grams (6 mmol) L-glutamic acid di-tertbutyl ester hydrochloride in 20 mL DCM. This solution is added dropwise over 45 minutes to a solution of 10 mL DCM and triphosgene (0.7 g, 2.2 mmol) at 0° C. After stirring an additional 30 min a solution of H-lys-(Z)—O-t-butyl ester HCl (2.2 g, 6 mmol) containing TEA (1.8 mL, 13 mmol) in 15 mL DCM was added in one portion. The solution was stirred for 1 hour. The reaction is concentrated, diluted with 50 mL ethyl acetate, washed 2N NaHSO4 (2×50 mL), brine (50 mL) and dried over sodium sulfate to yield a yellow oil. Purification by column chromatography to afford the desired product as a clear oil which upon standing solidifies to a white solid (1.9 g, 54%).

Route B. In a round bottom flask triphosgene (2.9 g, 10 mmol) is suspended in DCM (50 mL) and stirred at 0° C. A solution of H-Lysine(Z) freebase (9.1 g, 27 mmol) and DIEA (10.4 mL, 60 mmol) DCM (50 mL) was added dropwise to the triphosgene solution over 2.5 hours. After 2.5 hours a solution of L-gluetamic acid di-tertbutyl ester hydrochloride (8 g, 27 mmol) containing DIEA (10.4 mL, 60 mmol) DCM (50 mL) was added in one portion and allowed to stir for 45 minutes. The reaction was concentrated to dryness, diluted with 150 mL ethyl acetate, washed with 2N NaHSO₄ (2×200 mL), brine (150 mL) and dried over sodium sulfate to yield a yellow oil. This oil was purified by column chromatography (SiO₂) to afford the desired product as a clear oil which upon standing solidifies to a white solid (12.0 g, 72%). ¹H NMR (400 MHz, CDCl₃) δ7.34 (m, 5H), 5.33-5.28 (m, 3H), 5.08 (d,J=7.4 Hz, 2H), 4.38-4.29 (m, 2H), 3.15 (m, 2H), 2.32-2.01 (m, 2H), 1.90-1.50 (m, 8H), 1.43-1.40 (m, 27H, t-Bu's). ESMS m/z: 622 (M+H)⁺.

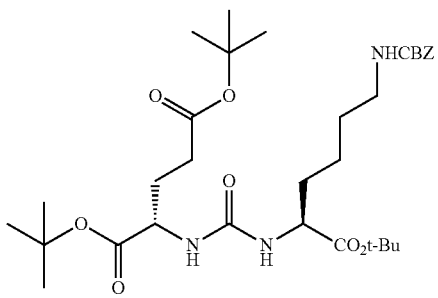

2-[3-(5-Amino-1-tert-butoxycarbonyl-pentyl)-ureido]pentanedioic acid di-tert-butyl ester (4)

To a solution of 2-[3-(5-Benzyloxycarbonylamino-1-tert-butoxycarbonyl-pentyl)-ureido]-pentanedioic acid di-tert-butyl ester (630 mg, 1.0 mmol) in ethanol (20 mL) was added ammonium formate (630 mg, 10 eqv) followed by 10% Pd-C and the suspension was allowed to stand with occasional agitation overnight until complete. The reaction was filtered through celite and concentrated to afford the desired product (479 mg, 98%) as a waxy solid. ¹H NMR (400 MHz, CDCl₃) δ7.15-6.0 (bm, 4H, NH's), 4.29 (m, 2H), 3.02 (m, 2H), 2.33 (m, 2H), 2.06-1.47 (m, 8H), 1.45-1.40 (m, 27H, t-Bu's). ESMS m/z: 488 (M+H)⁺.

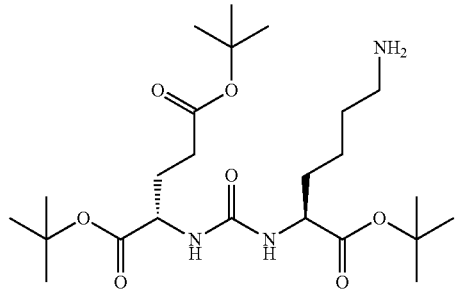 [SMILES: CC(C)(C)OC(=O)CC[C@H](NC(=O)N[C@@H](CCCCN)C(=O)OC(C)(C)C)C(=O)OC(C)(C)C]

Synthesis of the Glu-Urea-Clu Tether Core Model Compounds

In this series a tether is incorporated onto the side chain of glutamic acid or lysine prior to conjugation to form the urea dimer. In the example below the side chain carboxylic acid of one of the glutamic acids is modified into a tether to append a chelator, atom or functional group that is or contains a radionuclide (Scheme 4).

Scheme 4.

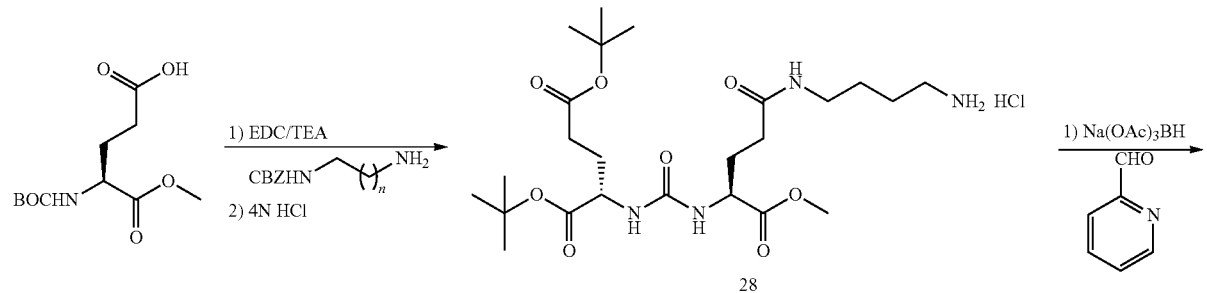

-continued

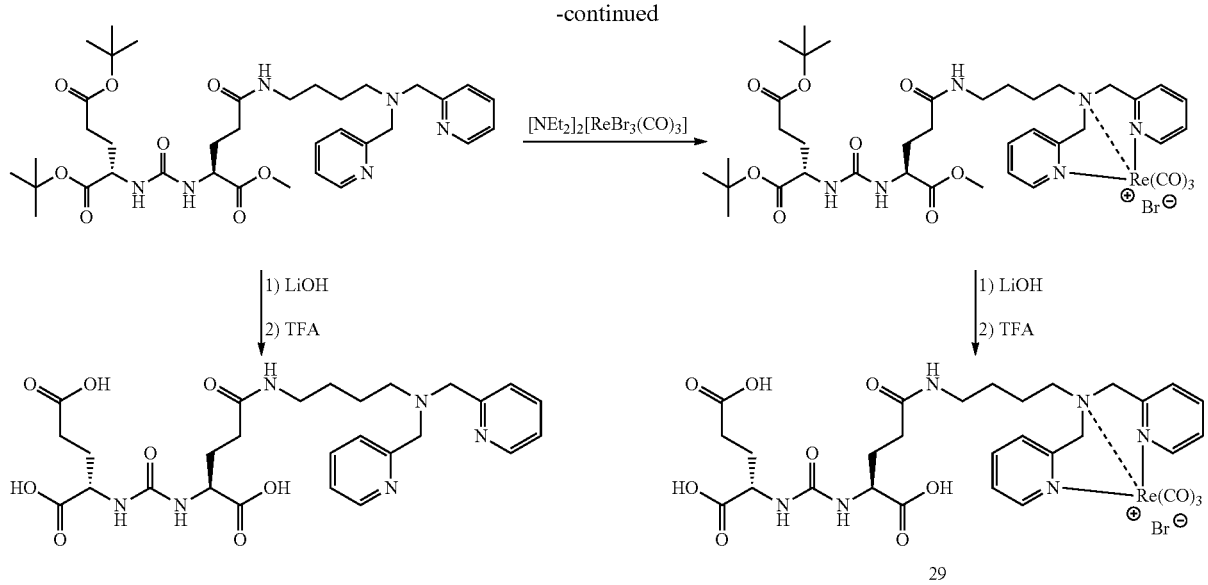

2-{3-[3-(4-Amino-butylcarbamoyl)-1-methoxycarbonyl-propyl]-ureido}-pentanedioic acid di-tertbutyl ester (28)

To a solution of N-BOC Glutamic acid α- methyl ester BOC-Glu(OH)-Ome (960 mg, 3.7 mmol) in DMF (6 mL) cooled to 0° C. was added EDC (845 mg, 1.3 eqv) and TEA (1.3 mL). After stirring for 10 min the mono protected diamine N-CBZ-1,4-diaminobutane hydrochloride salt (1 g, 3.8 mmol) was added and the reaction is allowed to stir overnight with warming to room temperature. The crude reaction was diluted with EA (100 mL) and washed with a washed with water (30 mL), 5% aq. Citric acid (30 mL), sat. sodium bicarbonate (30 mL), water (30 mL) and brine (30 mL). The organic layer was dried over sodium sulfate and concentrated to afford the crude product as a thick syrup (2.1 g). To the obtained syrup was added 4 N HCl in dioxane (10 mL) and the reaction was stirred at room temperature for 3 h. Concentration afforded a waxy solid (1.8 g) as the hydrochloride salt. The salt was coupled to the activated L-(S)-2-[(Imidazole-1-carbony)-amino]-pentanedioic acid di-tert-butyl ester (2) as described in the preceding experimental sections to afford the desired fully protected dimer x (1.9 g). This material was suspended in absolute EtOH (20 mL) excess ammonium formate (5 g) added followed by 20% Pd(OH)$_2$ on carbon (100 mg) and the suspension very gently agitated overnight to effect cleavage of the CBZ protection group. Filtration through celite and concentration afforded the desired free amine (1.4 g, 2.7 mmol, 73%, 4 steps). $^1$H NMR (400 MHz, CDCl$_3$) δ8.41 (br, 2H), 7.36 (br, 1H), 6.44 (bs, 1H), 6.37 (bs, 1H), 4.37-4.29 (m, 2H), 3.71 (s, 3H). 3.20-1.50 (m, 16H), 1.45 (s, 9H), 1.43 (s, 9H). ESMS m/z: 517 (M+H)$^+$.

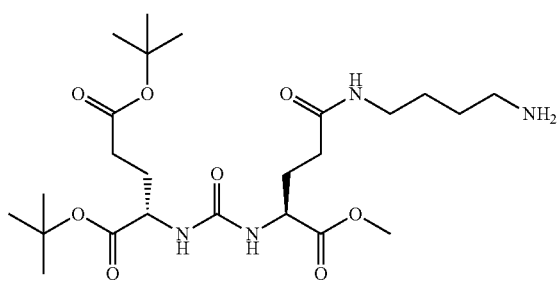 [SMILES: COC(=O)[C@H](CCC(=O)NCCCCN)NC(=O)N[C@@H](CCC(=O)OC(C)(C)C)C(=O)OC(C)(C)C]

Re(CO)$_3$-2-(3-{3-[4-(Bis-pyridin-2-ylmethyl-amino) butylcarbamoyl]-1-carboxy-propyl}- ureido)-pentanedioic acid[Br] (29) (MIP-1100)

The protected intermediate was prepared by reductive amination using pyridine-2-carboxaldehyde as previously described. Treatment with 2M LiOH in MeOH effected hydrolysis of the methyl ester. The methanol was removed and excess DCM:TFA (1:1) was added and the reaction stirred at room temperature overnight. The crude material was converted into the desired Rhenium conjugate following the procedure described above. Preparative HPLC afforded the desired molecule (9.5 mg. 16%). $^1$H NMR (400 MHz, DMSO-d$_6$) δ8.78 (m, 2H), 8.31 (br, 1H), 7.95 (m, 2H), 7.59 (m, 2H), 7.39 (m, 2H), 6.60-6.33 (m, 2H), 4.89 (m, 4H), 4.00 (m, 1H), 3.76 (m, 1H), 3.20-1.2 (m, 16H) (3 CO$_2$H not seen. ESMS 842 (M–H)$^+$.

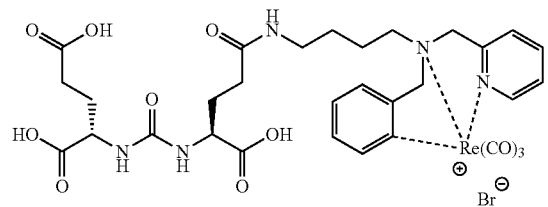

Synthesis of the Glu-urea-X-benzyl-Lysine Core Model Compounds

The following compounds were all prepared in overall yields ranging from 20-40% using the route depicted in Scheme 3. The Z-deprotected Glu-urea-lysine was mixed with the appropriate aldehyde (0.9 equivalents) at room temperature for one hour to form the ☐chiff base intermediate. The ☐chiff base was reduced using 1 equivalent of sodium triacetoxyborohydride. The compounds were deprotected using 50% TFA in DCM for 1 hour at room temperature. Upon completion, the reactions were concentrated on a rotary evaporator or were blown dry with nitrogen and extracted using methylene chloride and water. The water layer was evaporated to dryness to afford the deprotected product in 40-80% yield.

Scheme 3. General pathway for the synthesis of halogenated PSMA compounds.

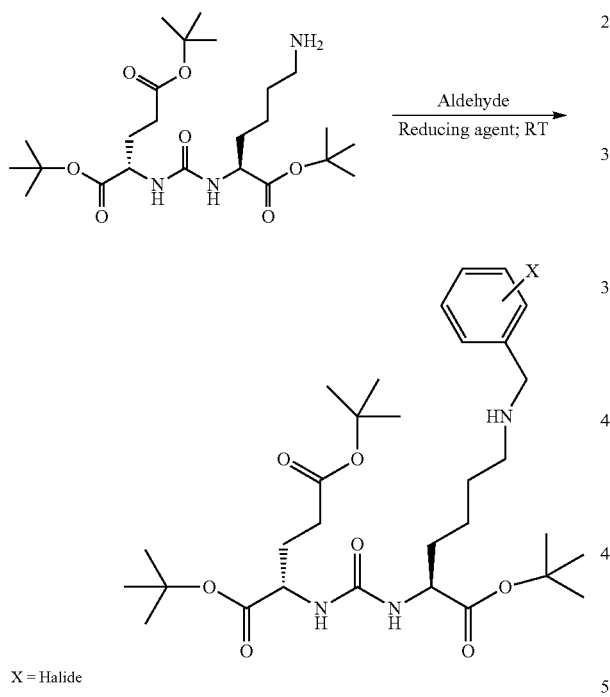

X = Halide

4-Trimethylstannanyl-benzaldehyde (5)

To a solution of 4-iodobenzaldehyde (1.92 g, 8.27 mmol) in dry dioxane (60 mL) was added hexamethylditin (4.1 mL, 19.8 mmol) followed by Pd(Ph$_3$P)Cl$_2$ (150 mg) and the reaction mixture was heated for 3 h under reflux until judged complete. The reaction was filtered through celite and purified by column chromatography using hexanes/ethyl acetate (9/1) as eluent to afford (2.24 g, 98%) as a clear oil. $^1$H NMR (400 MHz, CDCl$_3$) δ9.97 (s, 1H), 7.81 (d, J=7.8 Hz, 2H), 7.72 (d, J=7.8 Hz, 2H), 0.29 (s, 9H). ESMS m/z: 268 (Sn-cluster).

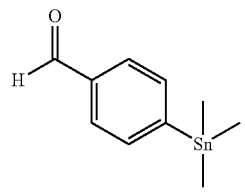

2-{3-[1-tert-Butoxycarbonyl-5-(4-trimethylstannanyl-benzylamino)-pentyl]-ureido}-pentanedioic acid di-tert-butyl ester (6)

To a solution of 2-[3-(5-Amino-1-tert-butoxycarbonyl-pentyl)-ureido]-pentanedioic acid di-tert-butyl ester (150 mg, 0.31 mmol) in DCE (10 mL) was added 4-Trimethylstannanyl-benzaldehyde (82 mg, 0.31 mmol) followed by sodium triacetoxyborohydride (98 mg, 0.47 mmol) and the reaction was stirred overnight at 40° C. The reaction was concentrated and purified by column chromatography using hexanes/ethyl acetate as eluent to afford the desired product (88 mg, 38%) as a thick syrup which begins to solidify upon standing. $^1$H NMR (400 MHz, DMSO-d$_6$) δ7.48 (d, J=7.4 Hz, 2H), 7.30 (d, J=7.4 Hz, 2H), 6.27 (m, 2H, NH's), 3.96 (m, 4H), 2.74 (bm, 2H), 2.21 (m, 2H), 1.87 (m, 2H), 1.65-1.19 (m, 7H), 1.35 (m, 27H, t-Bu's), 0.23 (s, 9H). ESMS m/z: 742 (Sn-cluster).

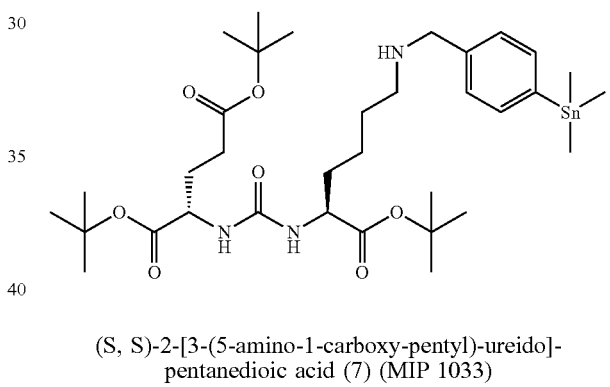

(S, S)-2-[3-(5-amino-1-carboxy-pentyl)-ureido]-pentanedioic acid (7) (MIP 1033)

The same experimental procedure as depicted in scheme 1, yielded 8% of 2-[3-(5-benzyloxycarbonylamino-1-tert-butoxycarbonyl-pentyl)-ureido]-pentanedioic acid di-tert-butyl ester. The compound was deprotected using the previously described methods and purified by HPLC to afford the desired product. $^1$H NMR (tri-t-butyl ester of Z-protected amine) (400 MHz, CDCl$_3$) δ12.2 (s, 3H), 6.4 (s, 2H), 4.15 (m, 2H), 3.45 (m, 1H), 2.75 (bs, 1H), 2.2 (m, 4H), 1.90 (m, 2H), 165 (m, 2H), 1.50 (s, 2H), 1.35 (m, 2H). ESMS m/z: 622 (M−H)$^+$.

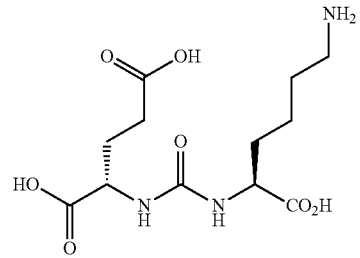 [SMILES: NCCCC[C@H](NC(=O)N[C@@H](CCC(=O)O)C(=O)O)C(=O)O]

(S)-2-(3,3-Bis-pyridin-2-ylmethyl-ureido)-pentanedioic acid (8) (MIP 1025)

The same experimental procedure as in the general synthesis, yielded 0.65 g, 48% of 2-(3,3-Bis-pyridin-2-ylmethyl-ureido)-pentanedioic acid di-tert-butyl ester. The compound was deprotected using the previously described methods and purified by HPLC to afford the desired product. $^1$H NMR (400 MHz, DMSO-$d_6$) δ, 12.0 (bs, 2H), 8.68 (d, 2H), 8.00 (m, 2H), 7.41 (d, 4H), 7.14 (d, 1H), 4.73 (d, 4H), 3.96 (s, 1H), 2.18 (m, 2H), 1.80 (m, 2H).

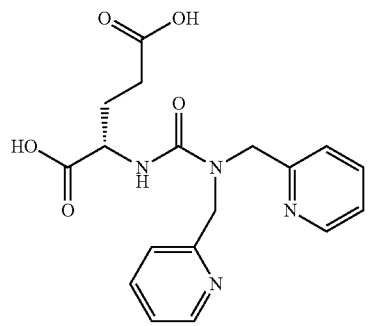 [SMILES: O=C(O)CC[C@H](NC(=O)N(Cc1ccccn1)Cc1ccccn1)C(=O)O]

(S,S)-2-{3-[3-(Bis-pyridin-2-ylmethyl-amino)-1-carboxy-propyl]-ureido}-pentanedioic acid (9) (MIP 1028)

The same experimental procedure as in the general synthesis in scheme 1, yielded 0.16 g, 35% of 2-{3-[3-(Bis-pyridin-2-ylmethyl-amino)-1-carboxy-propyl]-ureido}-pentanedioic acid di-tert-butyl ester. The compound was deprotected using the previously described methods and purified by HPLC to afford the desired product. $^1$H NMR (400 MHz, DMSO-$d_6$) δ12.4 (br, 2H), 9.37 (s, 1H), 8.52 (d, 2H), 7.80 (t, 2H), 7.14 (dd, 4H), 645 (m, 2H), 4.49 (br, 4H), 4.12 (s, 1H), 4.05 (s, 1H), 3.21 (m, 2H), 2.24 (m, 2H), 1.80 (m, 2H), 1.40 (m, 2H). ESMS m/z: (diethyl ester) 429 (M)$^+$, 451 (M+Na).

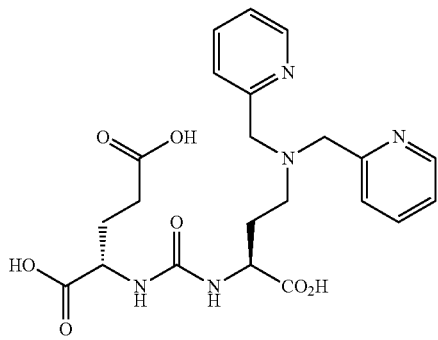 [SMILES: O=C(O)CC[C@H](NC(=O)N[C@@H](CCN(Cc1ccccn1)Cc1ccccn1)C(=O)O)C(=O)O]

(S,S)-2-{3-[5-(Bis-pyridin-2-ylmethyl-amino)-1-carboxy-pentyl]-ureido}-pentanedioic acid (10) (MIP 1008)

The same experimental procedure as in the general synthesis, yielded 0.09 g, 12% of 2-{3-[5-(Bis-pyridin-2-ylmethyl-amino)-1-carboxy-pentyl]-ureido}-pentanedioic acid di-tert-butyl ester. The compound was deprotected using the previously described methods and purified by HPLC to afford the desired product. $^1$H NMR (400 MHz, DMSO-$d_6$) δ12.7 (s, 2H), 8.97 (s, 1H), 8.65 (dd, 2H), 7.92 (dd, 2H), 7.45 (m, 4H), 6.44 (d, 1H), 6.28 (d, 1H), 4.45 (br, 4H), 4.10 (m, 2H), 3.15 (br, 2H), 2.60 (m, 2H), 2.25 (m, 2H), 1.90 (m, 2H), 1.78 (m, 2H), 1.45 (m, 2H).

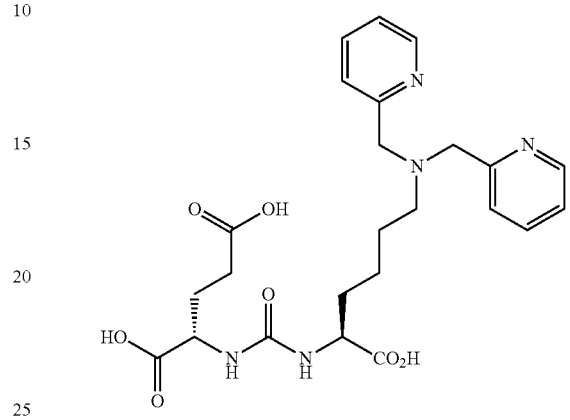

(S)-2-{3-[1-Carboxy-2-(4-iodo-phenyl)-ethyl]-ureido}-pentanedioic acid (11) (MIP-1034)

The same experimental procedure as in the general synthesis, yielded 0.038 g, 5% of 2-{3-[1-Carboxy-2-(4-iodo-phenyl)-ethyl]-ureido}-pentanedioic acid di-tert-butyl ester. The compound was deprotected using the previously described methods. $^1$H NMR (400 MHz, DMSO-$d_6$) δ12.40 (s, 3H), 7.65 (dd, 2H), 7.05 (dd, 2H), 6.30 (m, 2H), 4.25 (s, 1H), 4.05 (s, 1H), 2.90 (m, 2H), 2.2 (m, 2H), 1.80 (m, 2H). ESMS m/z: 429 (M)$^+$, 451 (M+Na).

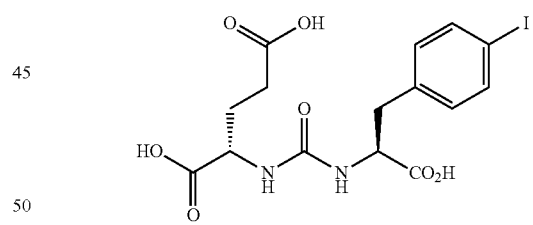

(S, S)-2-{3-[1-Carboxy-5-(2-iodo-benzylamino)-pentyl]-ureido}-pentanedioic acid (12) (MIP 1035)

The same general procedure, using the previously prepared and protected 2-[3-(5-Amino-1-carboxy-pentyl)-ureido]-pentanedioic acid di t-butyl ester. The compound was deprotected using the previously described methods (5.5 mg, 66%). $^1$H NMR (400 MHz, DMSO-$d_6$) δ12.4 (s, 3H), 8.8 (s, 1H), 7.94 (m, 1H), 7.5 (m, 1H), 7.16 (t, 1H), 6.38 (m, 2H), 4.15 (m, 5H), 3.06 (s, 2H), 2.85 (s, 1H), 2.2 (m, 2H), 1.90 (m, 1H), 1.70 (m, 2H), 1.50 (s, 2H), 1.35 (m, 2H). ESMS m/z: 536 (M+H)$^+$.

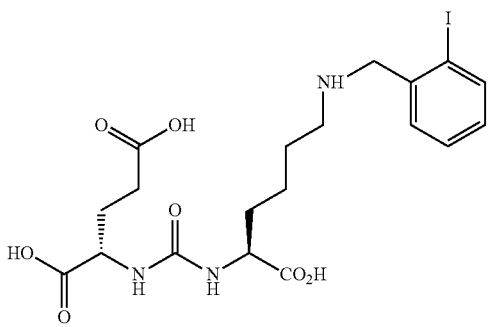

(S, S)-2-{3-[1- Carboxy-5-(3-iodo-benzylamino)-pentyl]-ureido}-pentanedioic (13) (MIP 1089)

The same general procedure, using previously prepared and protected 2-[3-(5-Amino-1-carboxy-pentyl)-ureido]-pentanedioic acid di t-butyl ester. The compound was deprotected using the previously described methods (4.1 mg, 53%). $^1$H NMR (400 MHz, DMSO-$d_6$) δ12.4 (s, 3H), 8.7 (s, 2H), 7.9 (s, 1H), 7.8 (d, 1H), 7.44 (d, 1H), 7.22 (t, 1H), 6.25 (s, 2H), 4.09 (m, 5H), 2.89 (s, 1H), 2.75 (s, 1H), 2.2 (d, 2H), 1.90 (m, 2H), 1.65 (m, 2H), 1.40 (m, 2H).

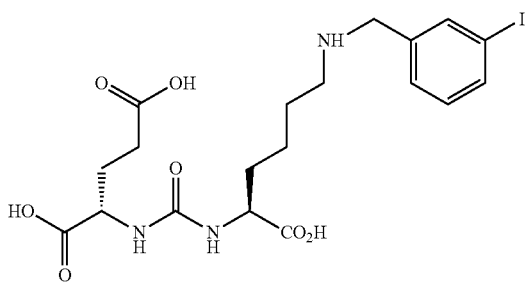 [SMILES: O=C(O)CC[C@H](NC(=O)N[C@@H](CCCCNCc1cccc(I)c1)C(=O)O)C(=O)O]

(S, S)-2-{3-[1- Carboxy-5-(4-iodo-benzylamino)-pentyl]-ureido}-pentanedioic (14) (MIP 1072)

The same general procedure, using previously prepared and protected 2-[3-(5-Amino-1-carboxy-pentyl)-ureido]-pentanedioic acid di t-butyl ester. The compound was deprotected using the previously described methods (12 mg, 66%), $^1$H NMR (400 MHz, DMSO-$d_6$) δ12.4 (bs, 3H), 8.8 (br, 1H), 7.8 (d, 2H), 7.27 (d, 2H), 6.35 (br, 2H), 4.1 (m, 4H), 2.89 (m, 2H), 2.2 (d, 2H), 1.90 (m, 2H), 1.65 (m, 4H), 1.35 (m, 2H). ESMS m/z: 536 (M+H)$^+$.

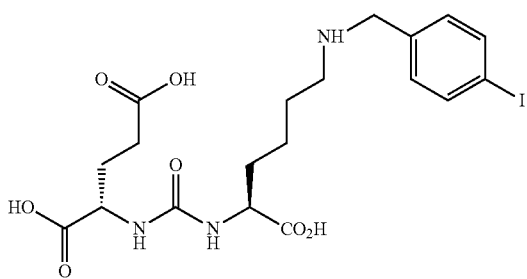 [SMILES: O=C(O)CC[C@H](NC(=O)N[C@@H](CCCCNCc1ccc(I)cc1)C(=O)O)C(=O)O]

(S, S)-2-{3-[1- Carboxy-5-(4-fluoro-benzylamino)-pentyl]-ureido}-pentanedioic (15) (MIP 1090)

The same general procedure, using previously prepared and protected 2-[3-(5-Amino-1-carboxy-pentyl)-ureido]-pentanedioic acid di t-butyl ester. The compound was deprotected using the previously described methods. $^1$H NMR (400 MHz, DMSO-$d_6$) δ12.4 (br, 3H), 8.7 (br, 1H), 7.5 (m, 2H), 7.3 (m, 2H), 6.35 (m, 2H), 4.1 (m, 4H), 2.9 (m, 2H), 2.2 (d, 2H), 1.90 (m, 2H), 1.60 (m, 4H), 1.35 (m, 2H). ESMS m/z: 428 (M+H)$^+$, 450 (M+Na).

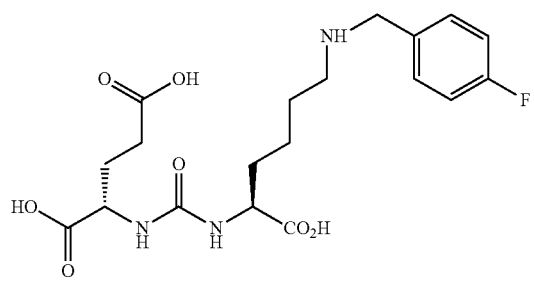 [SMILES: O=C(O)CC[C@H](NC(=O)N[C@@H](CCCCNCc1ccc(F)cc1)C(=O)O)C(=O)O]

(S, S)-2-{3-[1- Carboxy-5-(4-bromo-benzylamino)-pentyl]-ureido}-pentanedioic (16) (MIP 1094)

The same general procedure, using previously prepared and protected 2-[3-(5-Amino-1-carboxy-pentyl)-ureido]-pentanedioic acid di t-butyl ester. $^1$HNMR (tri t-butyl ester) (400 MHz, CDCl$_3$) δ7.52 (d, 2H), 7.32 (d, 2H), 6.28 (m, 2H), 3.98 (m, 2H), 2.55 (t, 2H), 2.48 (t, 2H), 2.22 (m, 2H), 1.85 (m, 2h), 1.62 (m, 2H), 1.45 (m, 2H), 1.37 (s, 27H), 1.28 (m, 2H) ESMS m/z: 642 (M+H)$^+$. The compound was deprotected using the previously described methods. ESMS m/z: 474 (M+H)$^-$.

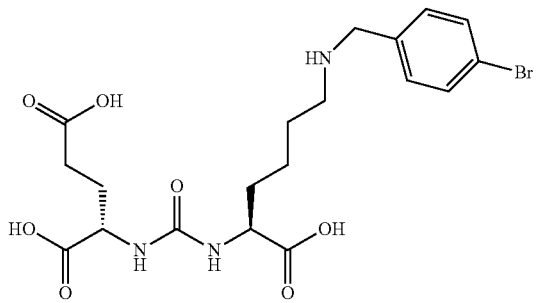 [SMILES: O=C(O)CC[C@H](NC(=O)N[C@@H](CCCCNCc1ccc(Br)cc1)C(=O)O)C(=O)O]

(S, S)-2-{3-[1- Carboxy-5-(4-iodo-benzylamino)-pentyl]-ureido}-pentanedioic acid (17) (MIP 1044)

The same general procedure, using previously prepared and protected 2-[3-(5-Amino-1-carboxy-pentyl)-ureido]-pentanedioic acid di t-butyl ester. The compound was deprotected using the previously described methods. $^1$H NMR (400 MHz, DMSO-$d_6$) δ12.4 (s, 3H), 8.45 (s, 1H), 7.8 (dd, 2H), 7.6 (dd, 2H), 6.3 (s, 2H), 5.75 (s, 1H), 4.1 (m, 4H), 3.2 (s, 2H), 2.25 (d, 2H), 1.90 (m, 1H), 1.65 (m, 2H) 1.4 (m, 2H).

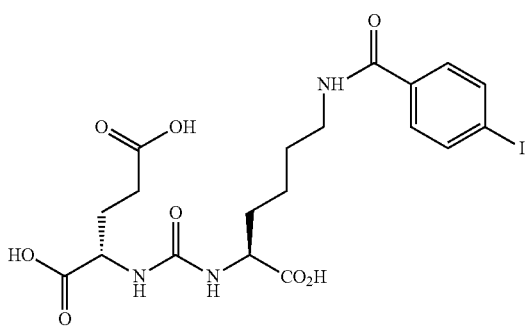 [SMILES: O=C(O)CC[C@H](NC(=O)N[C@@H](CCCCNC(=O)c1ccc(I)cc1)C(=O)O)C(=O)O]

2-{3-[1-carboxy-5-(4-iodo-benzenesulfonylamino)-pentyl]-ureido}-pentanedioic acid (18) (MIP 1097)

In a round bottom flask 2-[3-(5-Amino-1-carboxy-pentyl)-ureido]-pentanedioic acid di t-butyl ester (300 mg, 0.62 mmol) is suspended in water (10 mL) and 1,4 dioxane (10 mL) and TEA (1.75 mL, 1.25 mmol) was added followed by 4-iodo-benzenesulfonyl chloride and the mixture stirred overnight at 50° C. The reaction mixture was evaporated to dryness, taken up in DCM and chromatographed over silica gel to afford the desired product (375 mg, 80%) as a clear oil. The compound was deprotected using the previously described methods followed by HPLC purification to afford the desired product MIP-1097 as a whiter solid (270 grams, 90% yield). $^1$H NMR (400 MHz, DMSO-$d_6$) δ7.97 (d, 2H), 7.68 (t, 1H), 7.53(d, 2H), 6.35 (dd, 2H), 4.10 (m, 1H), 4.00 (m, 1H), 2.65 (m, 2H), 2.22 (m, 2h), 1.9 (m, 1H), 1.7 (m, 1H), 1.55 (m, 1H), 1.45 (m, 1H), 1.35 (m, 2H), 1.25 (m, 2H), (3 $CO_2H$ not seen). ESMS m/z: 565 (M+H)$^+$.

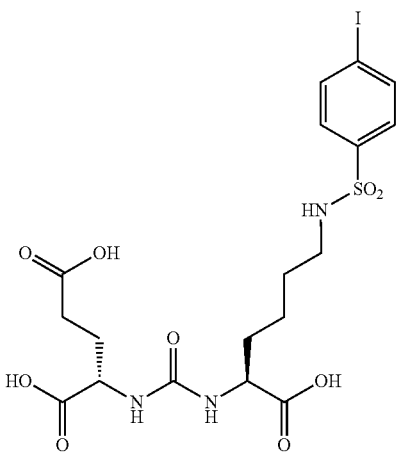 [SMILES: O=C(O)CC[C@H](NC(=O)N[C@@H](CCCCNS(=O)(=O)c1ccc(I)cc1)C(=O)O)C(=O)O]

2-(3-{1-Carboxy-5-[3-(4-iodo-phenyl)-ureido]-pentyl}-ureido)-pentanedioic acid (19) (MIP 1095)

In a round bottom flask 4-iodo-phenyl isocyante (100 mg, 0.41 mmol) is dissolved in DCM (10 mL) containing TEA (0.057 mL, 0.4 mmol). 2-[3-(5-Amino-1-carboxy-pentyl)-ureido]-pentanedioic acid di t-butyl ester (200 mg, 0.41 mmol) was added and stirred for 3 hours. The reaction mixture was evaporated to dryness and the crude mixture taken up in methanol (5 mL). Dropwise addition to water (20 mL) afforded a white precipitate which was collected and washed with water (20 mL) and dried to afford the desired tri-tert butyl ester as a white solid which was deprotected directly using the previously described method to afford the desired product (158 mg, 53%) as a white solid. $^1$H NMR (400 MHz, DMSO-$d_6$) δ8.51 (s, 1H), 7.5 (d, 2H), 7.22 (d, 2H), 6.3 (t, 2H), 6.16 (t, 1H), 4.05 (m, 2H), 3.05 (m, 2H), 2.24 (m, 2H), 1.0 (m, 1H), 1.68 (m, 24H), 1.52 (m, 1H), 1.38 (m, 2H), 1.28 (m, 2H), 3 $CO_2H$ not seen). ESMS m/z: 565 (M+H)$^+$.

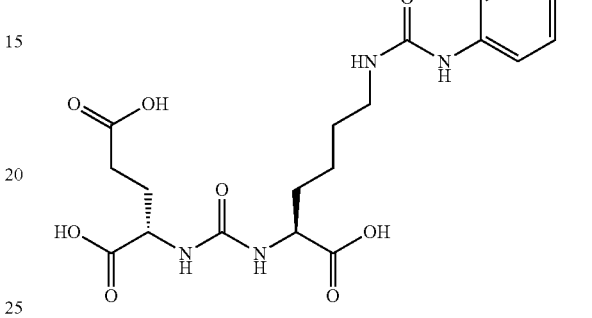

Synthesis of Glu-Urea-β-Phenyl Glycines (±) 3-Amino-3-(3-iodo-phenyl)-propionic acid (20)

Malonic acid (2.2 g, 21.5 mmol) and 3-iodobenzaldehyde (5 g, 21.5 mmol) were suspended in ethanol (50 mL) and ammonium acetate (1.66 g, 21.5 mmol) was added and the reaction heated to a reflux overnight. The reaction was cooled to room temperature filtered and washed with ethanol followed by ether and dried to afford the product (3.4 g, 11.6 mmol, 54%) as a white solid. $^1$H NMR (400 MHz, DMSO-$d_6$) δ7.80 (s, 1H), 7.64 (dd, J=7.8 Hz, 1H), 7.42 (dd, J=7.6 Hz, 1H), 7.16 (dd, J=7.8 Hz, 1H), 7.14 (dd, J=7.6 Hz, 1H), 4.21 (m, 1H), 2.36 (m, 2H).

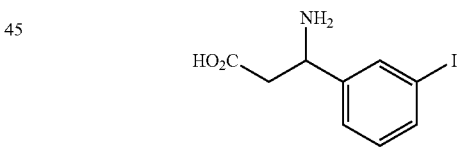

(±) 3-Amino-3-(3-iodo-phenyl)-propionic acid methyl ester (21)

To a suspension of (±) 3-Amino-3-(3-iodo-phenyl)-propionic acid (3.1 g, 10.6 mmol) in methanol was added thionyl chloride (0.95 mL, 12.7 mmol) and the reaction was stirred at room temperature overnight. Concentration followed by trituration with ether gives a white solid. The solid is filtered, washed with ether and dried to afford the desired product (3.5 g, 10 mmol, 95%) as a white solid. $^1$H NMR (400 MHz, DMSO-$d_6$) δ8.79 (br, 2H), 8.01 (s, 1H), 7.74 (d, J=8.1 Hz, 1H), 7.57 (d, J=7.8 Hz, 1H), 7.21 (dd, J=8.1, 7.8 Hz, 1H), 4.56 (br, 1H), 3.54 (s, 3H), 3.23-3.17 (m, 1H), 3.04-2.98 (m, 1H).

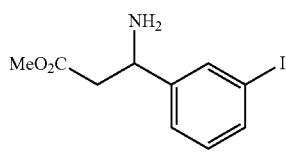 [SMILES: COC(=O)CC(N)c1cccc(I)c1]

(S, R) and (S, S)-2-{3-[1-(3-Iodo-phenyl)-2-methoxycarbonyl-ethyl]-ureido}-pentanedioic acid di-tert-butyl ester (22)

2-[(Imidazole-1-carbonyl)-amino]-pentanedioic acid di-tert-butyl ester (370 mg, 1.05 mmol) was dissolved in DCE (10 mL) and cooled to 0° C. MeoTf (142 μL, 1.25 mmol) was added and the reaction was allowed to proceed for 20 min. (±)3-Amino-3-(3-iodo-phenyl)-propionic acid methyl ester (356 mg, 1.045 mmol) was added and the reaction was allowed to warm to room temperature and then warmed to 55° C. and stirred overnight. The reaction was diluted with DCM (50 mL) and washed with water (30 mL), 5% aq. Citric acid (30 mL), sat. sodium bicarbonate (30 mL), water (30 mL) and brine (30 mL). The organic layer was dried over sodium sulfate and concentrated to afford the crude product. The product was purified by column chromatography to afford the desired product (303 mg, 0.51 mmol, 49%) as a white foam. $^1$H NMR (400 MHz, CDCl$_3$) δ7.66 (s, 1H), 7.57 (d, J=7.6 Hz, 1H), 7.29 (s, 1H), 7.07-7.02 (m, 1H), 5.74 (br, 1H), 5.17 (br, 2H), 4.30 (m, 1H), 3.63 (s, 1.5H), 3.62 (s, 1.5H), 2.88-2.76 (m, 2H), 2.38-2.24 (m, 2H), 2.10-2.00 (m, 1H), 1.90-1.80 (m, 1H), 1.46 (s, 9H), 1.44 (s, 9H).

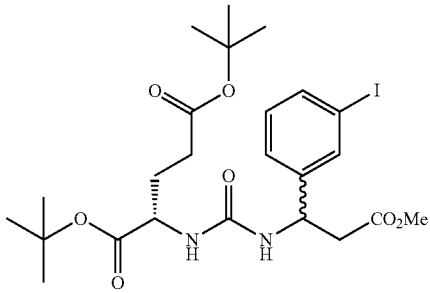 [SMILES: COC(=O)CC(NC(=O)N[C@@H](CCC(=O)OC(C)(C)C)C(=O)OC(C)(C)C)c1cccc(I)c1]

(S, R) and (S, S)-2-{3-[2-Carboxy-1-(3-iodo-phenyl)-ethyl]-ureido}-pentanedioic acid (23)

To a solution of (±)2-{3-[1-(3-Iodo-phenyl)-2-methoxycarbonyl-ethyl]-ureido}-pentanedioic acid di-tert-butyl ester (289 mg, 0.49 mmol) was dissolved in methanol (3 mL) and 2M LiOH (0.5 mL) was added and the reaction stirred at room temperature overnight. The reaction was diluted with water (20 mL) and the organic layer was extracted with ethyl acetate (2×20 mL) then acidified with 1N HCl to pH ~2. The aqueous layer was extracted with ethyl acetate (3×20 mL), dried over sodium sulfate and concentrated to afford the crude product (206 mg, 0.36 mmol, 73%) as a white solid. To the crude material was added DCM (2 mL) followed by TFA (2 mL) and the reaction was stirred at room temperature overnight. Concentration followed by recrystallization from ethyl acetate afforded the desired product (22 mg, 0.047 mmol, 10%) as a white solid. $^1$H NMR (400 MHz, DMSO-d$_6$) δ12.39 (br, 3H), 7.64 (br, 1H), 7.56 (m, 1H), 7.30 (bm, 1H), 7.10 (bm, 1H), 6.72 (bm, 1H), 6.34 (bm, 1H), 4.94 (br, 1H), 4.03 (bm, 1H), 2.64 (br, 2H), 2.20 (br, 2H), 1.86 (br, 1H), 1.71 (br, 1H). ESMS m/z: 463 (M−H)$^+$.

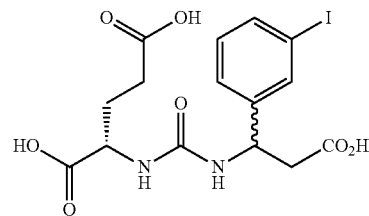 [SMILES: O=C(O)CC[C@H](NC(=O)NC(CC(=O)O)c1cccc(I)c1)C(=O)O]

(S, S)-2-{3-[1-Carboxy-5-(2-chloro-benzylamino)-pentyl]-ureido}-pentanedioic (7) (MIP-1137)

The same general procedure as shown in Scheme 1, using previously prepared and protected 2-[3-(5-Amino-1-carboxy-pentyl)-ureido]-pentanedioic acid di-t-butyl ester. The compound was deprotected using the previously described methods to yield the desired product (100 mg, 45%) as an off-white solid. $^1$H NMR (400 MHz, DMSO-d$_6$) δ9.0 (br, 3H), 7.63 (d, 1H), 7.2 (m, 2H), 7.15 (d, 1H), 6.30 (d, 2H), 4.1 (m, 4H), 2.9 (br, 2H), 2.2 (m, 2H), 1.90 (m, 2H), 1.60 (m, 4H), 1.35 (m, 2H). ESMS m/z: 444 (M+H)$^+$.

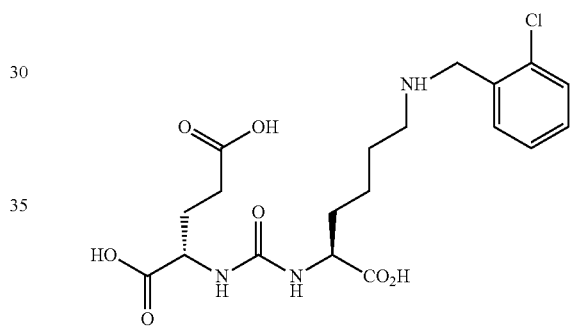

(S, S)-2-{3-[1-Carboxy-5-(3-chloro-benzylamino)-pentyl]-ureido}-pentanedioic (8) (MIP 1131)

The same general procedure as shown in Scheme 1, using previously prepared and protected 2-[3-(5-Amino-1-carboxy-pentyl)-ureido]-pentanedioic acid di t-butyl ester. The compound was deprotected using the previously described methods to yield the desired product (200 mg, 90%) as an off-white solid. $^1$H NMR (400 MHz, DMSO-d$_6$) δ8.9 (br, 3H), 7.6 (s, H), 7.43 (m, 3H), 6.39 (br, 2H), 4.1 (m, 4H), 2.9 (br, 2H), 2.2 (m, 2H), 1.90 (m, 2H), 1.60 (m, 4H), 1.35 (m, 2H). ESMS m/z: 444 (M+H)$^+$.

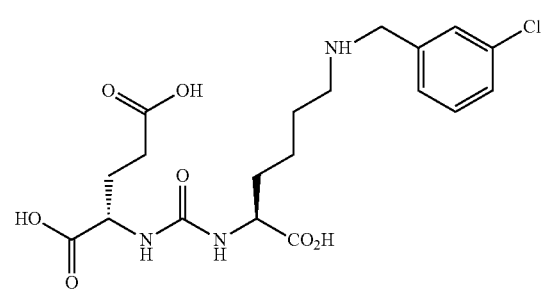 [SMILES: O=C(O)CC[C@H](NC(=O)N[C@@H](CCCCNCc1cccc(Cl)c1)C(=O)O)C(=O)O]

(S, S)-2-{3-[1-Carboxy-5-(4-chloro-benzylamino)-pentyl]-ureido}-pentanedioic (9) (MIP 1135)

The same general procedure as shown in Scheme 1, using previously prepared and protected 2-[3-(5-Amino-1-carboxy-pentyl)-ureido]-pentanedioic acid di t-butyl ester. The compound was deprotected using the previously described methods to yield the desired product (10 mg, 66%) as an off-white solid. ESMS m/z: 444 (M+H)+.

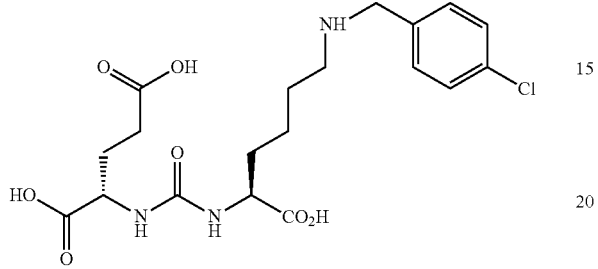

(S)-2-(3-((R)-5-(benzylamino)-1-carboxypentyl)ureido)pentanedioic acid (10) (MIP-1106)

The same general procedure as shown in Scheme 1, using previously prepared and protected 2-[3-(5-Amino-1-carboxy-pentyl)-ureido]-pentanedioic acid di t-butyl ester. The compound was deprotected using the previously described methods to yield the desired product (5 mg, 47%) as an off-white solid. ESMS m/z: 410 (M+H)+.

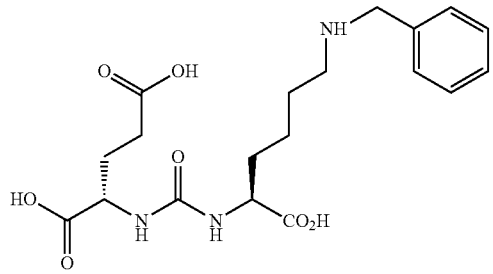 [SMILES: O=C(O)CC[C@H](NC(=O)N[C@@H](CCCCNCc1ccccc1)C(=O)O)C(=O)O]

2-(3-{1-Carboxy-5-[3-(phenyl)-ureido]-pentyl}-ureido)-pentanedioic acid (11) (MIP 1111)

In the round bottom flask phenyl isocyanate (100 mg, 0.84 mmol) was dissolved in DCM (10 mL) 2-[3-(5-Amino-1-carboxy-pentyl)-ureido]-pentanedioic acid di t-butyl ester (409 mg, 0.84 mmol) was added and stirred for 3 hours. The reaction mixture was evaporated to dryness and the crude mixture was purified via flash column chromatography 2:1 hexanes/ethyl acetate to afford the tert-butyl ester as a white solid which was deprotected using TFA/CH2Cl2 affording the desired product. 1H NMR (400 MHz, DMSO-d6) δ12.5 (s, 3H), 8.54 (s, 1H), 7.40 (dd, 2H), 7.26 (dd, 2H), 6.30 (t, 2H), 6.17 (t, 1H), 4.05 (m, 2H), 3.05 (m, 2H), 2.44 (m, 2H), 1.90 (m, 1H), 1.68 (m, 2H), 1.52 (m, 1H), 1.40 (m, 2H), 1.29 (m, 2H). ESMS m/z: 439 (M+H)+.

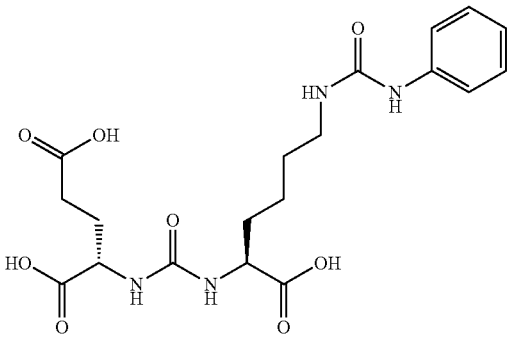 [SMILES: O=C(O)CC[C@H](NC(=O)N[C@@H](CCCCNC(=O)Nc1ccccc1)C(=O)O)C(=O)O]

2-(3-{1-Carboxy-5-[3-(4-bromo-phenyl)-ureido]-pentyl}-ureido)-pentanedioic acid (12) (MIP 1129)

In the round bottom flask 4-bromo-phenyl isocyanate (100 mg, 0.50 mmol) was dissolved in DCM (10 mL). 2-[3-(5-Amino-1-carboxy-pentyl)-ureido]-pentanedioic acid di t-butyl ester (246 mg, 0.50 mmol) was added and stirred for 3 hours. The reaction mixture was evaporated to dryness and the crude mixture was purified via flash column chromatography 2:1 hexanes/ethyl acetate to afford the tert-butyl ester as a white solid which was deprotected using TFA/CH2Cl2 affording the desired product.
1H NMR (400 MHz, DMSO-d6) δ12.5 (s, 3H), 8.55 (s, 1H), 7.35 (d, 4H), 6.30 (t, 2H), 6.18 (t, 1H), 4.08 (m, 2H), 3.05 (m, 2H), 2.22 (m, 2H), 1.90 (m, 1H), 1.68 (m, 2H), 1.52 (m, 1H), 1.40 (m, 2H), 1.30 (m, 2H). ESMS m/z: 518 (M+H)+.

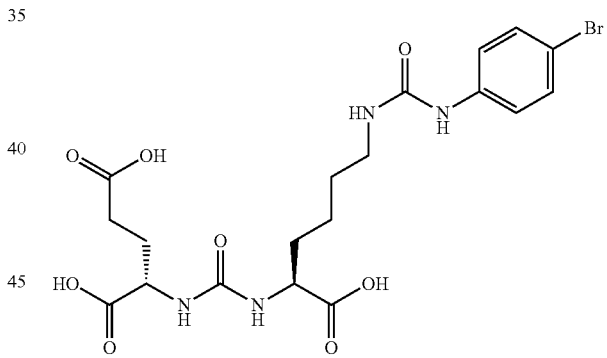

2-(3-{1-Carboxy-5-[3-(4-chloro-phenyl)-ureido]-pentyl}-ureido)-pentanedioic acid (13)(MIP 1110)

In the round bottom flask 4-bromo-phenyl isocyanate (100 mg, 0.65 mmol) was dissolved in DCM (10 mL) 2-[3-(5-Amino-1-carboxy-pentyl)-ureido]-pentanedioic acid, di-t-butyl ester (318 mg, 0.65 mmol) was added and stirred for 3 hours. The reaction mixture was evaporated to dryness and the crude mixture was purified via flash column chromatography 2:1 hexanes/ethyl acetate to afford the tert-butyl ester as a white solid (470 mg, 96%) which was deprotected using TFA/CH2Cl2 affording the desired product.
1H NMR (400 MHz, DMSO-d6) δ12.5 (s, 3H), 8.35 (s, 1H), 7.40 (dd, 2H), 7.19 (dd, 2H), 6.30 (t, 2H), 6.10 (t, 1H), 4.08 (m, 2H), 3.05 (m, 2H), 2.32 (m, 2H), 1.90 (m, 1H), 1.68 (m, 2H), 1.52 (m, 1H), 1.40 (m, 2H), 1.30 (m, 2H). ESMS m/z: 474 (M+H)+.

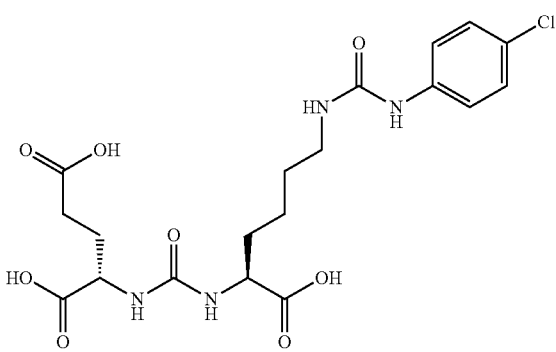 [SMILES: O=C(O)CC[C@H](NC(=O)N[C@@H](CCCCNC(=O)Nc1ccc(Cl)cc1)C(=O)O)C(=O)O]

(S)-2-(3-((R)-1-carboxy-5-(☐yridine☐ne-1-ylmethylamino)pentyl)ureido)pentanedioic acid (14) (MIP-1108)

The same general procedure as shown in Scheme A, using previously prepared and protected 2-[3-(5-Amino-1-carboxy-pentyl)-ureido]-pentanedioic acid di t-butyl ester. The compound was deprotected using the previously described methods to yield the desired product (51 mg, 70%) as an off-white solid. $^1$H NMR (400 MHz, DMSO-d$_6$) δ8.9 (br, 3H), 7.95 (m, 5H), 7.6 (m, 2H), 6.35 (br, 2H), 4.1 (m, 4H), 2.9 (br, 2H), 2.55 (m, 2H), 2.25 (m, 2H), 1.70 (m, 4H), 1.3 (m, 2H). ESMS m/z: 460 (M+H)$^+$.

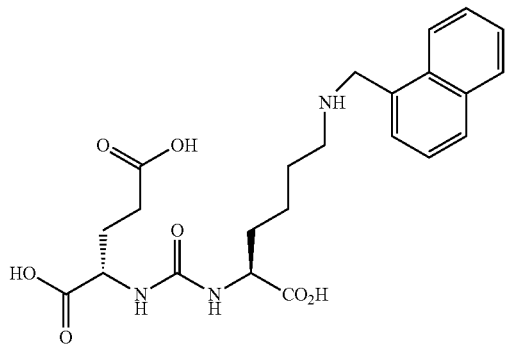 [SMILES: O=C(O)CC[C@H](NC(=O)N[C@@H](CCCCNCc1cccc2ccccc12)C(=O)O)C(=O)O]

2-(3-{1-Carboxy-5-[3-(3-iodo-benzyl)-ureido]-pentyl}-ureido)-pentanedioic acid (15) (MIP-1101)

The same general procedure as shown in Scheme 2, using previously prepared and protected 2-[3-(5-Amino-1-carboxy-pentyl)-ureido]-pentanedioic acid di t-butyl ester. The compound was deprotected using the previously described methods to yield the desired product. ESMS m/z: 579 (M+H)$^+$.

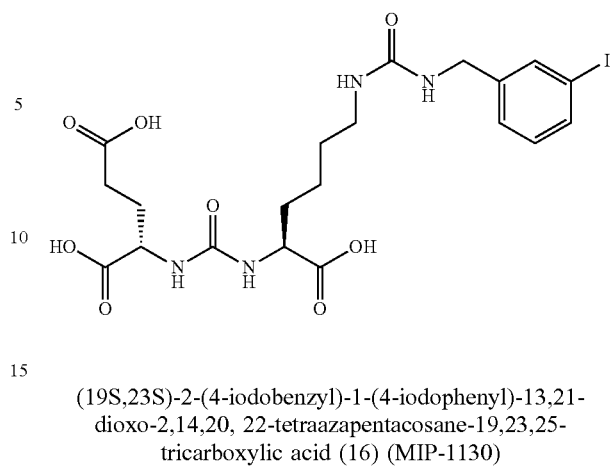

(19S,23S)-2-(4-iodobenzyl)-1-(4-iodophenyl)-13,21-dioxo-2,14,20, 22-tetraazapentacosane-19,23,25-tricarboxylic acid (16) (MIP-1130)

The same general procedure as shown in Scheme A, using previously prepared and protected 2-[3-(5-Amino-1-carboxy-pentyl)-ureido]-pentanedioic acid di t-butyl ester. The compound was deprotected using the previously described methods to yield the desired product (8.3 mg, 10%) as an off-white solid. $^1$H NMR (400 MHz, DMSO-d$_6$) δ7.8 (d), 7.3 (d), 6.3 (dd), 4.25 (br), 4.05 (m), 2.97 (m), 2.85 (br), 2.22 (m), 2.05 (m), 0.90 (m), 1.64 (m), 1.48 (m), 1.35 (m), 1.2 (m). ESMS m/z: 936 (M+H)$^+$.

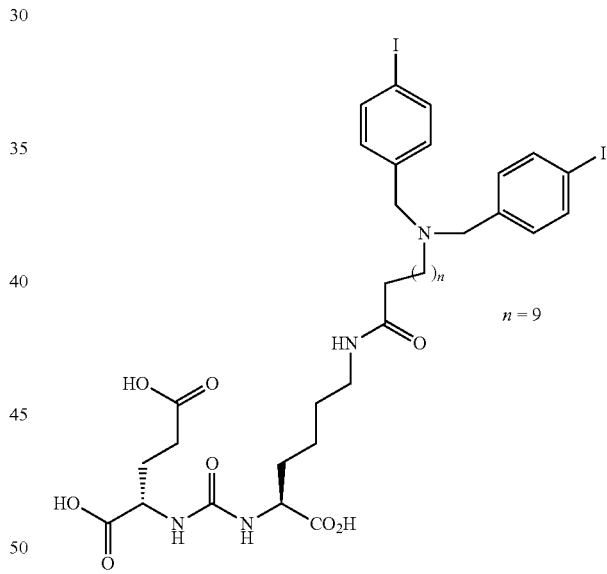

Rhenium General Experimental

The rhenium complexes of the SAAC-inhibitors are conveniently isolated from the reactions of the readily available precursor [Net$_4$]$_2$[Re(CO)$_3$Br$_3$] with the SAAC-inhibitor. Since the donor sets provided by the SAAC terminus are well documented as effective chelators for the {M(CO)$_3$}$^{+1}$ core and have been designed to adopt the required facial arrangement about the metal site, the preparations of the complexes were unexceptional.

The {Re(I)(CO)$_3$}$^+$ system followed similar reaction chemistry to that of the Tc-99m tricarbonyl core. The use of [Net$_4$]$_2$[ReBr$_3$(CO)$_3$], as the starting material led to facile formation of the fac-{Re(CO)$_3$(L)$_3$} core. The [Net$_4$]$_2$[ReBr$_3$(CO)$_3$] was readily derived from the [ReBr(CO)$_5$]. The synthesis of the Re(I) complexes was accomplished by reacting [Net$_4$]$_2$[ReBr$_3$(CO)$_3$] with the appropriate TEC ligand in the ratio of 1:1.2 in 10 ml of methanol. The reaction was allowed to heat at 80° C. for 4 hours. After cooling all of the following reaction products were all purified using a small silica column with yields ranging from 10-30%.

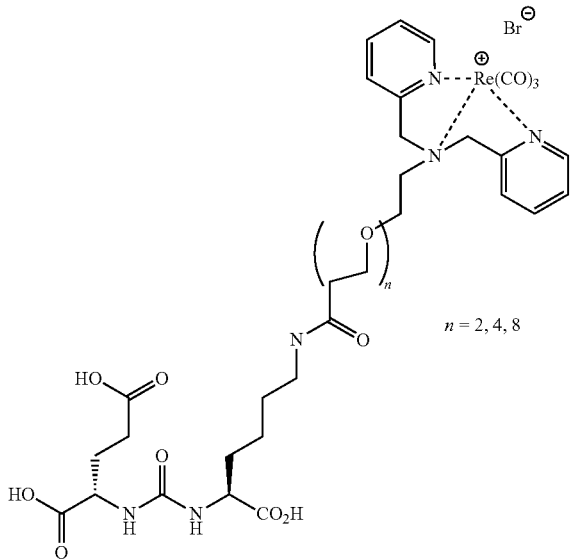

Glu-urea-Lys-PEG2-ReDP:

[Re(CO)$_3${(17R,21S)-11,19-dioxo-1-(☐yridine-2-yl)-2-(☐yridine-2-ylmethyl)-5,8-dioxa-2,12,18,20-tetraazatricosane-17,21,23-tricarboxylic acid}][Br]. (17) (MIP -1133)

The PEG2 dipyridyl compound, (17R,21S)-11,19-dioxo-1-(☐yridine-2-yl)-2-(☐yridine-2-ylmethyl)-5,8-dioxa-2,12,18,20-tetraazatricosane-17,21,23-tricarboxylic acid was prepared employing the same general procedure as shown in Scheme 1, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (2 mg, 20%) as an off-white solid. $^1$H NMR (400 MHz, DMSO-d$_6$) δ8.8 (d), 8.00 (dd), 7.55 (d), 7.42 (dd), 6.45 (s), 3.95 (m), 3.4-3.6 (m), 2.45 (m), 1.25 (m), 1.1 (m), 0.8 (m). ESMS m/z: 931 (M+H)$^+$.

Glu-urea-Lys-PEG4-ReDP:

[Re(CO)$_3${(23R,27S)-17,25-dioxo-1-(pyridine-2-yl)-2-(pyridine-2-ylmethyl) -5,8,11,14-tetraoxa-2,18,24,26-tetraazanonacosane-23,27,29-tricarboxylic acid}] [Br]. (18) (KM11-200)

The PEG4 dipyridyl compound (23R,27S)-17,25-dioxo-1-(pyridine-2-yl)-2-(pyridine-2-ylmethyl)-5, 8,11,14-tetraoxa-2,18,24,26-tetraazanonacosane-23,27,29-tricarboxylic acid was prepared employing the same general procedure as shown in Scheme A, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product. (5.1 mg, 29.6%) as an white solid. ESMS m/z: 1019 (M+H)$^+$.

Glu-urea-Lys-PEG8-ReDP:

[Re(CO)$_3${(35R,39S)-29,37-dioxo-1-(☐yridine-2-yl)-2-(☐yridine-2-ylmethyl) -5,8,11,14,17,20,23,26-octaoxa-2,30,36,38-tetraazahentetracontane-35,39,41-tricarboxylic acid}][Br]. (19) (MIP-1132)

The PEG8 dipyridyl compound, (35R,39S)-29,37-dioxo-1-(pyridine-2-yl)-2-(pyridine-2-ylmethyl) -5,8,11,14,17,20,23,26-octaoxa-2,30,36,38-tetraazahentetracontane-35,39,41-tricarboxylic acid was prepared employing the same general procedure as shown in Scheme A, using previously prepared and protected 2-[3-(5-Amino-1-carboxy -pentyl)-ureido]-pentanedioic acid di t-butyl ester. The rhenium ester complex was prepared employing the same procedure as described in the general rhenium experimental. The compound was deprotected using the previously described methods to yield the desired product (8.0 mg, 30.4%) as an white solid. ESMS m/z: 1195 (M+H)$^+$.

Glu-urea-Lys-C11PAMA-Re:

[Re(CO)$_3${(19R,23S)-13,21-dioxo-2-(☐yridine-2-ylmethyl)-2,14,20,22-tetraazapentacosane-1,19,23,25-tetracarboxylic acid}] (20) (MIP-1109)

The C11-PAMA compound, (19R,23S)-13,21-dioxo-2-(☐yridine-2-ylmethyl)-2,14,20,22-tetraazapentacosane-1, 19,23,25-tetracarboxylic acid was prepared employing the same general procedure as shown in Scheme A, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (3.0 mg, 75%) as an off-white solid. ESMS m/z: 922 (M+H)$^+$.

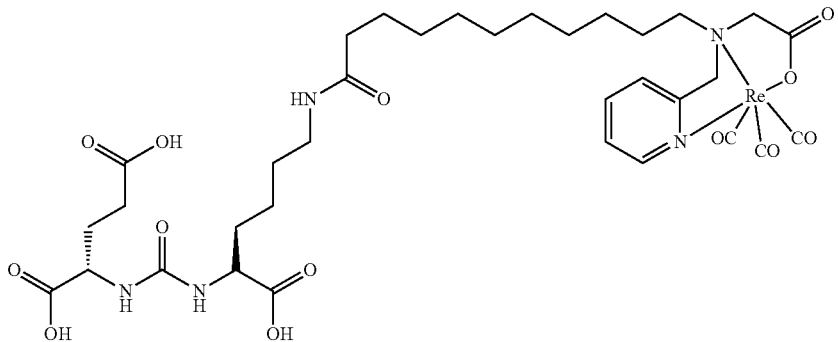

-continued

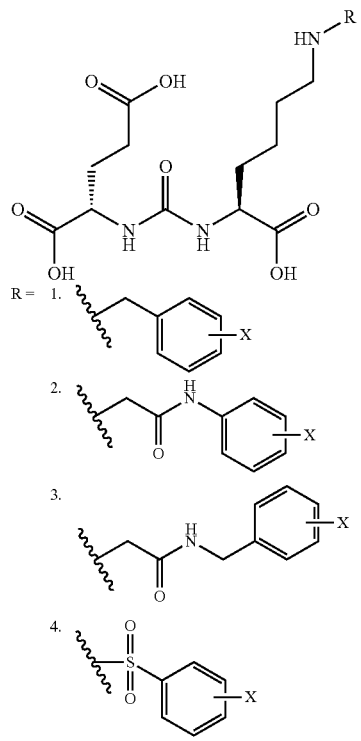

R = 1. [benzyl-X]
2. [anilide-X]
3. [benzylamide-X]
4. [sulfonyl-phenyl-X]
5. H

X = I, Br, Cl, F, H

Table 1 below is a summary of synthesized PSMA inhibitors investigated.

TABLE 1

Table 1. Summary of in vitro cell binding data of the additional or retested Glu-Urea-Lys derivatives.

| MIP # | X | Compound Description | IC$_{50}$ (uM) |
|---|---|---|---|
| — | — | PMPA | 10 |
| 1033 | — | Glu-urea-Lys | 498 |
| 1137 | 2-Cl | 2-Cl-benzyl | 245 |
| 1131 | 3-Cl | 3-Cl-benzyl | 277 |
| 1135 | 4-Cl | 4-Cl-benzyl | 2 |
| 1106 | H | Des-halo benzyl | 2960 |
| 1111 | H | Des-halo diurea | 12 |
| 1129 | 4-Br | 4-Br-diurea | 2 |
| 1110 | 4-Cl | 4-Cl-diurea | 4 |
| 1108 | — | 2-naphyl | 154 |
| 1101 | 3-I | 3-I-diurea | 10 |
| 1130 | 4-di-I | C11 4-di-iodo | 300 |
| 1133 | — | PEG2Re | 227 |
| KM11-200 | — | PEG4Re | NA |
| 1132 | — | PEG8Re | 1747 |
| 1109 | — | C11PAMA-Re | 696 |
| 1027 | 4-I | 4-I-benzoyl | 3* |
| 1095 | 4-I | 4-I-diurea | 10* |

β-Amino Acid Analogs

β-amino acid analogs of MIP-1072, MIP-1095, MIP-1027 specifically but the extension to other analogs such as the technetium conjugates as well as other halogen analogs is very desirable. We have no new examples to support this claim at this time.

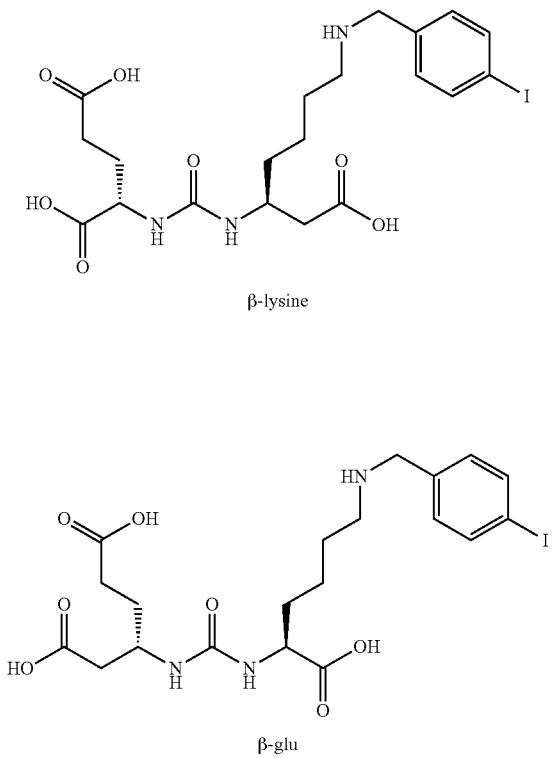

MIP-1072 β-amino acid analogs

β-lysine

β-glu

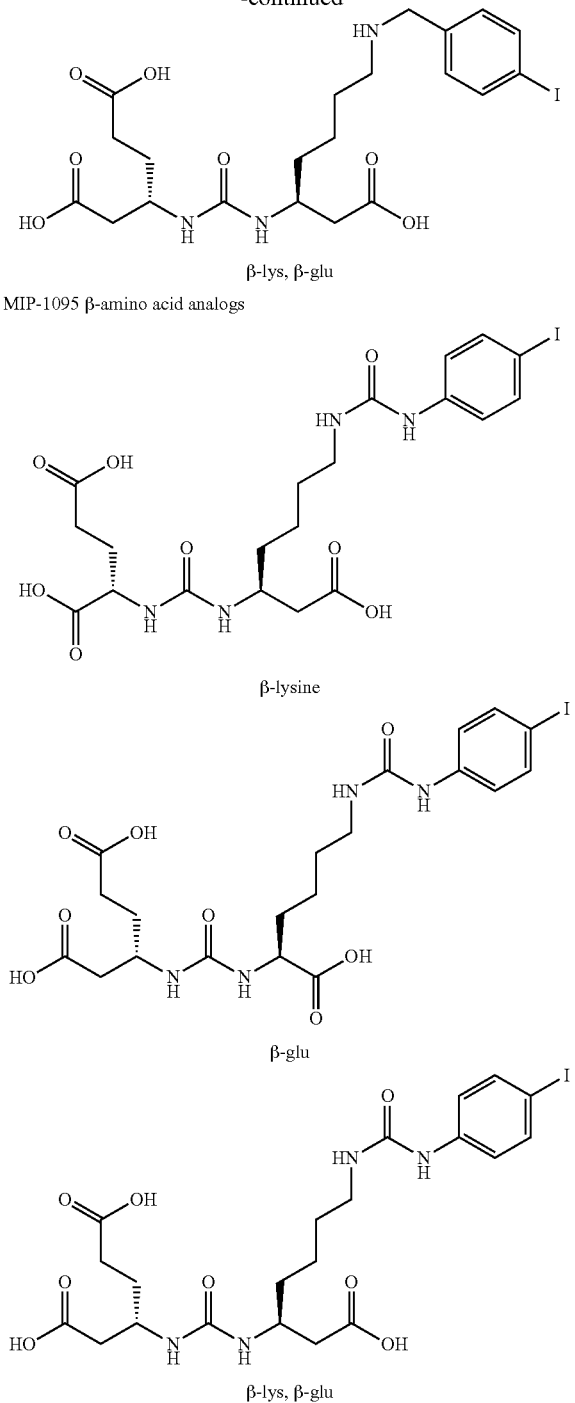

MIP-1095 β-amino acid analogs

β-lys, β-glu

β-lysine

β-glu

β-lys, β-glu

Synthesis of {Re(CO)₃}⁺¹ Core Model Complexes

The properties of the Group VII metals technetium and rhenium are very similar due to their periodic relationship. It was anticipated that the metals would demonstrate similar reaction chemistry, which is often the case for the tricarbonyl, nitrogen, and thiazole chemistry of these two metals. Likewise, due to their similar size that stabilizes the spin paired d⁶ electron configuration of M(I), perrhenate and pertechetate have very similar reaction behaviors. Synthesizing the rhenium-TECs allowed us a facile route to structurally characterize the products. The periodic relationship between Tc and Re indicates the Tc-99m radiopharmaceuticals can be designed by modeling analogous rhenium complexes.

Some of the new compounds were synthesized with macroscopic quantities of rhenium for characterization by conventional methods, including mass-spectrometry, ³H and ¹³C NMR spectrometry. Following purification, the synthesized rhenium complexes were run through a HPLC column for purification and identification of retention times to compare with Tc reaction products. The rhenium-TEC complexes were also crystallized.

The rhenium complexes of the SAAC-inhibitors are conveniently isolated from the reactions of the readily available precursor {Re(CO)₃(H₂O)₃}⁺¹ and [Net₄]₂[Re(CO)₃Br₃] with the SAAC-inhibitor. Since the donor sets provided by the SAAC terminus are well documented as effective chelators for the {M(CO)₃}⁺¹ core and have been designed to adopt the required facial arrangement about the metal site, the preparations of the complexes were unexceptional.

General Experimental

The {Re(I)(CO)₃}⁺ system followed similar reaction chemistry to that of the Tc-99m tricarbonyl core. The use of [Net₄]₂[ReBr₃(CO)₃], as the starting material led to facile formation of the fac-{Re(CO)₃(L)₃} core. The [Net₄]₂[ReBr₃(CO)₃] was readily derived from the [ReBr(CO)₅]. The synthesis of the Re(I) complexes was accomplished by reacting [Net₄]₂[ReBr₃(CO)₃] with the appropriate TEC ligand in the ratio of 1:1.2 in 10 ml of methanol. The reaction was allowed to heat at 80° C. for 4 hours. After cooling all of the following reaction products were all purified using a small silica column with yields ranging from 10-30%.

[Re(CO)₃(2-{3-[3-(Bis-pyridin-2-ylmethyl-amino)-1-carboxy-propyl]-ureido}-pentanediethyl ester)][Br] (24)

¹H NMR (400 MHz, DMSO-d₆) δ8.65 (dd, 2H), 7.85 (dd, 2H), 7.7 (dd, 4H), 7.25 (dd, 2H), 6.42 (dd, 1H), 6.0 (dd, 1H), 4.5 (m, 2H), 4.16 (m, 2H), 3.80 (m, 4H), 2.45 (m, 2H), 2.0 (dd, 2H), 1.5 (m, 4H), 1.25 (m, 6H). ESMS m/z: 812-815.

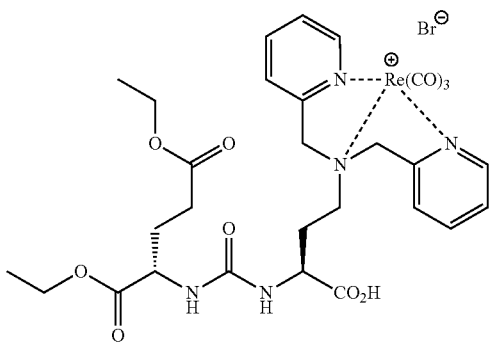

[Re(CO)₃(2-{3-[5-(Bis-pyridin-2-ylmethyl-amino)-1-carboxy-pentyl]-ureido}-pentanedioic acid)][Br] (25) (MIP 1029)

¹H NMR (400 MHz, DMSO-d₆) δ12.6 (s, 2H), 8.91 (s, 1H), 8.63 (dd, 2H), 7.85 (dd, 2H), 7.75 (dd, 4H), 7.3 (dd, 2H), 6.44 (d, H), 6.28 (d, 1H), 4.45 (s, 2H), 4.10 (m, 2H), 3.15 (s, 1H), 2.60 (m, 2H), 2.25 (m, 2H). 1.90 (m, 1H), 1.78 (m, 2H), 1.45 (m, 2H). ESMS m/z: 770-774.

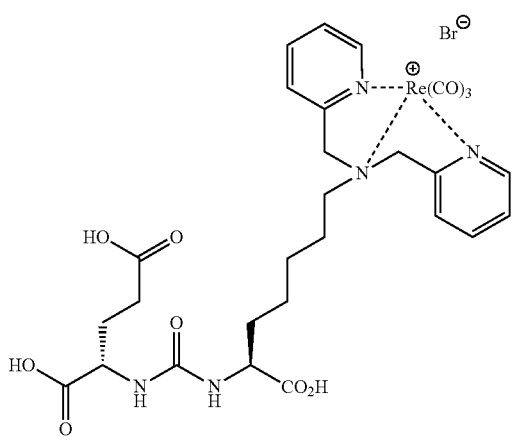

2-{3-[1-Carboxy-5-(carboxymethyl-pyridin-2-ylm-ethyl-amino)-pentyl]-ureido}-pentanedioic acid (26)

The same general procedure, using previously prepared and protected 2-[3-(5-Amino-1-carboxy-pentyl)-ureido]-pentanedioic acid di t-butyl ester. The compound was deprotected using the previously described methods (2.2 mg, 65%). $^1$H NMR (400 MHz, DMSO-$d_6$) δ8.65 (d, 1H), 7.91 (dd, 1H), 7.56 (d, 1H), 7.45 (dd, 1H), 6.31 (m, 2H), 4.34 (s, 2H), 4.08 (m, 4H), 3.10 (m, 2H), 2.24 (m, 2H), 1.95 (m, 1H), 1.68 (m, 4H), 1.5 (m, 1H), 1.22 (m, 2H). ESMS m/z: 469 (M+H)$^+$. M+1 469.

[Re(CO)$_3$(2-{3-[1-Carboxy-5-(carboxymethyl-pyridin-2-ylmethyl-amino)-pentyl]-ureido}pentanedioic acid)] (27)

$^1$H NMR (400 MHz, DMSO-$d_6$) δ8.75 (d, 1H), 8.13 (dd, 1H), 7.69 (d, 1H), 7.57 (dd, 1H), 6.45 (m, 2H), 4.75 (m, 1H), 4.50 (m, 1H), 4.20 (m, 2H), 3.61 (m, 4H), 3.15 (m, 2H), 2.38 (m, 1H), 2.0 (m, 2H), 1.75 (m, 4H), 1.62 (m, 1H), 1.25 (m, 2H). ESMS m/z 779-782 (M+2Na)$^+$.

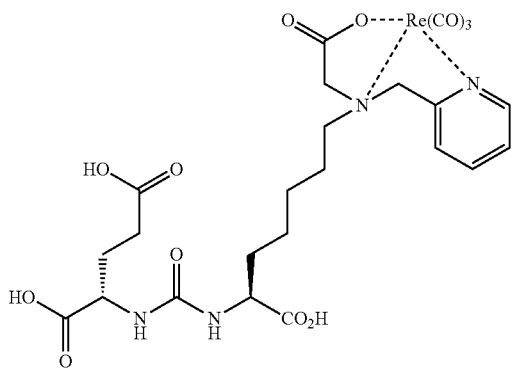

Synthesis of Glu-Urea-Lys(N-benzyl-X) Analogs (3).

The compounds of the general structure 3 were prepared in overall yields ranging from 20-40% using the general route depicted in Scheme A. The key synthetic intermediate (1) was reacted with the appropriate aldehyde at room temperature in for one hour to form the ☐yridi base intermediate. The ☐yridi base was not isolated but was reduced in situ with sodium triacetoxyborohydride. The t-butyl ester protecting groups were removed using 50% TFA in DCM for 1 hour at room temperature. Upon completion of the deprotection, the reactions were concentrated on a rotary evaporator and purified by HPLC or flash chromatography to afford the desired products (3) in 40-80% yield.

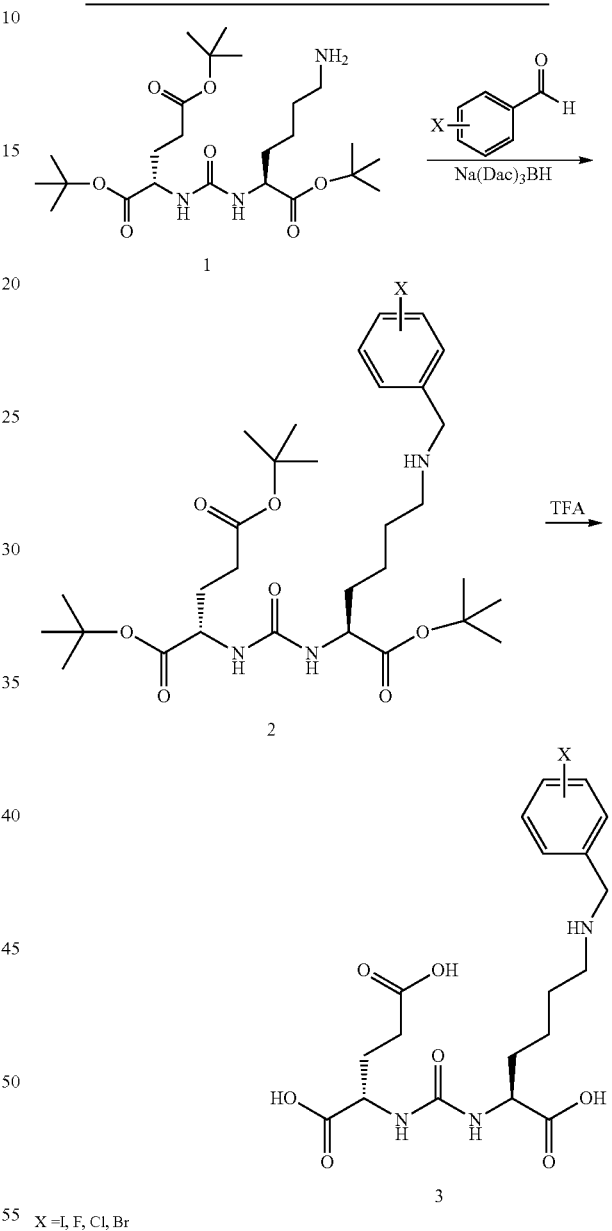

Scheme A. General pathway for the synthesis of halogenated Glu-Ura-Lys(N-benzyl-X) analogs (3).

X =I, F, Cl, Br

Synthesis of Glu-Urea-Ureido(Phenyl-X) Analogs

The compounds of the general structure 8 were prepared in overall yields ranging from 20-60% by the route depicted in Scheme B. The key synthetic intermediate (4) was reacted with the appropriate phenylisocyanate at room temperature to afford the desired protected intermediates (5) in good yields. The t-butyl ester protecting groups were removed in the presence of 50% TFA in DCM for 1 hour at room temperature. Upon completion, the reactions were concentrated on a rotary evaporator purified by HPLC or recrystallization to afford the desired products (6) in 40-90% yield.

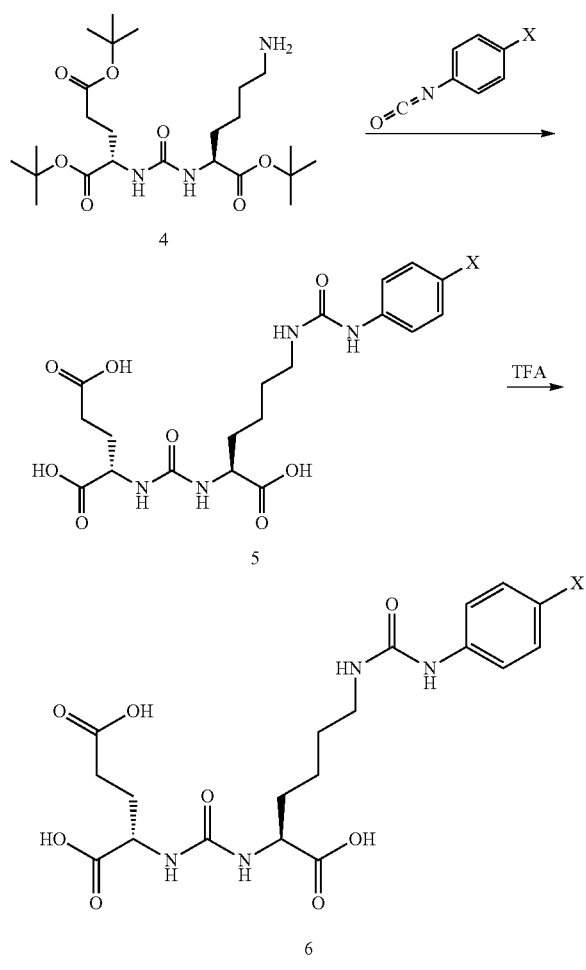

Scheme B. General pathway for the synthesis of halogenated Glu-Urea-Ureido(Phenyl-x) analogs.

X = I, F, Cl, Br

Preparation and Characterization of the Radio-labeled Complexes

Technetium-99m Labeling

Preparation of the $^{99m}$Tc-labeled complexes were achieved by addition of 100 μL of a solution containing [$^{99m}$Tc(CO)$_3$(H$_2$O)$_3$]$^+$ to 500 μL of 10$^-$ M solutions of the inhibitor-SAAC. The mixtures were heated at 70° C. for 30 min. The products were analyzed for their radiochemical purity by reverse-phase HPLC.

The stability of the radiolabeled compounds in solution and in serum were determined as a function of time and solution conditions. Specifically, after radiolabeling and isolation, the product was stored at room temperature for 6 h after which HPLC analysis was performed to check for degree of label retention, as well as potential product degradation. The reformation of TcO$_4^-$ and the presence of the reduced material TcO$_2$ was analyzed.

To assist in predicting the in vivo stability, ligand challenges were performed. Specifically, the stabilities of the $^{99m}$Tc complexes were investigated by incubating the HPLC purified complexes in 5% mouse serum at room temperature and 37° C. The ability of competing ligands, such as cysteine and DTPA, to extract Tc-99m from the complexes was studied by incubating the purified complexes with solutions (PBS pH 7.2) containing competing ligands at final concentrations of 0.1 M.

The results of the labeling competition studies demonstrated no degradation of the Tc-99m-complexes out to 6 hours in the serum or the competing ligands study. The results of the incubation at 37° C. after 6 hours are shown in FIG. 2.

Iodinations of DCT

Preparation of the iodine-131 labeled compound N-[N-[(S)-1,3-dicarboxypropyl]carbamoyl]-S-3-iodo-L-tyrosine (I-131-DCIT) was achieved by addition of 100 ul of [I-131] NaI in 0.1 N NaOH to a PBS (pH 7.2) solution containing DCT (1 mg/mL) in an Iodogen tube™ (Fisher Scientific, Pierce). The mixture was vortexed for 3 minutes and stored at room temperature for 20 minutes.

Figure 3A:
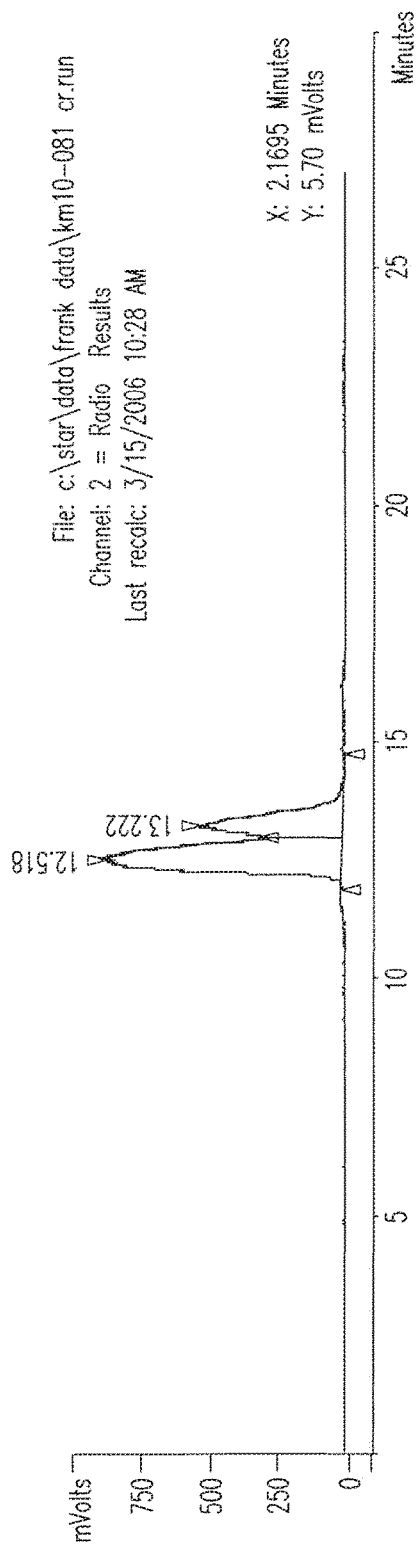
FIGS. 3A-3B are respective HPLC chromatograms of N-[N-[(S)-1, 3-dicarboxypropyl]carbamoyl]-S-3-iodo-L-tyrosine (I-131 DCIT) crude reaction FIG. 3A, top, purified at 2 hours, FIG. 3B, middle and at 2 days FIG. 3C, bottom.
Figure 3B:
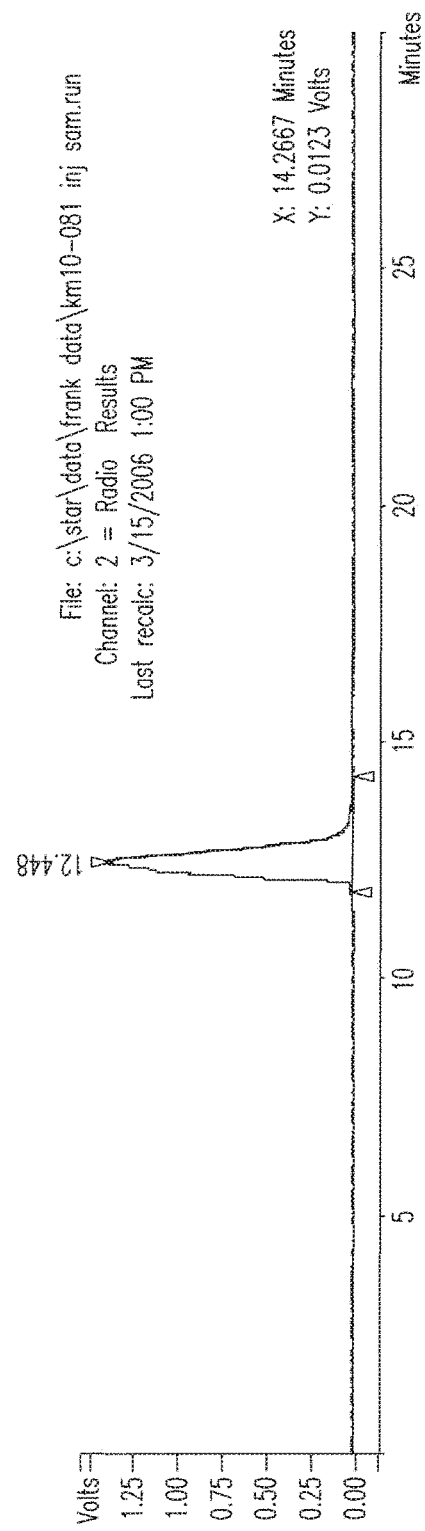
Figure 3C:
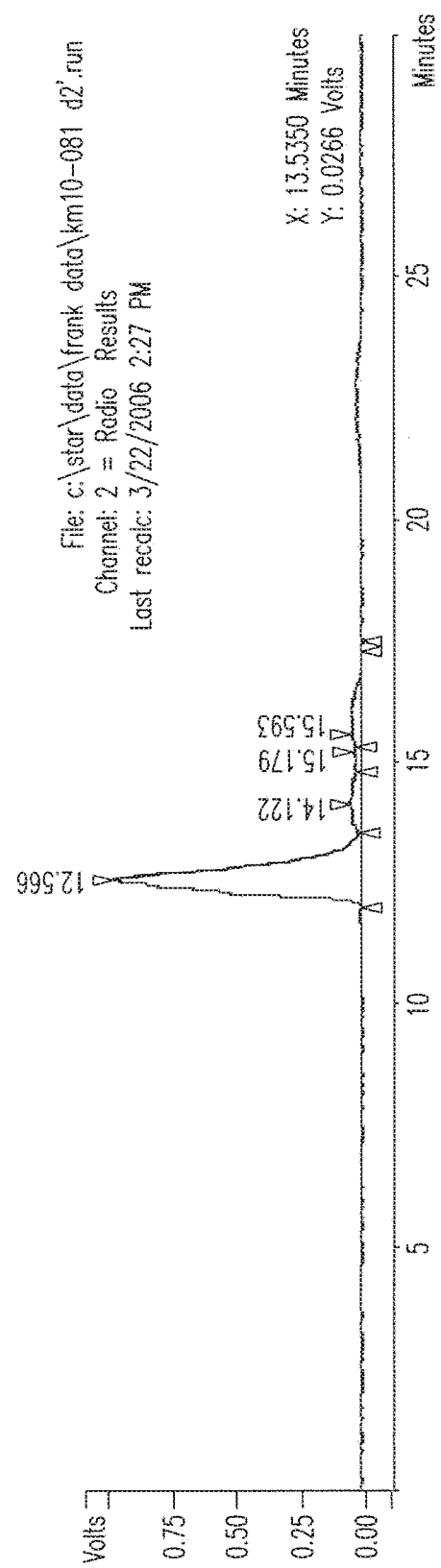

The stability of the radiolabeled compound in solution was determined as a function of time. Specifically, after radiolabeling and isolation, the product was stored at room temperature for 48 h after which HPLC analysis was performed to check for degree of label retention, as well as potential product degradation. The reformation of NaI and the presence of the reduced iodates was analyzed. The results of the labeling stability study demonstrated not significant degradation of the I-131 DCIT out of 2 days at room temperature. The results of the study are shown in FIG. 3.

Preparation of the iodine-131 labeled compound 2-{3-[1-Carboxy-5-(4-iodo-benzoylamino)-pentyl]-ureido}-pentanedioic acid (I-131-MIP 1072) was achieved by addition of 100 ul of [I-131] NaI in 0.1 N NaOH with 30 μl methanol with 0.5% acetic acid to a PBS (pH 7.2) solution containing MIP 1072 (1 mg/mL) in an IODOGEN TUBE (Fisher Scientific). The mixture was vortexed for 3 minutes and stored at room temperature for 20 minutes.

Figure 4C:
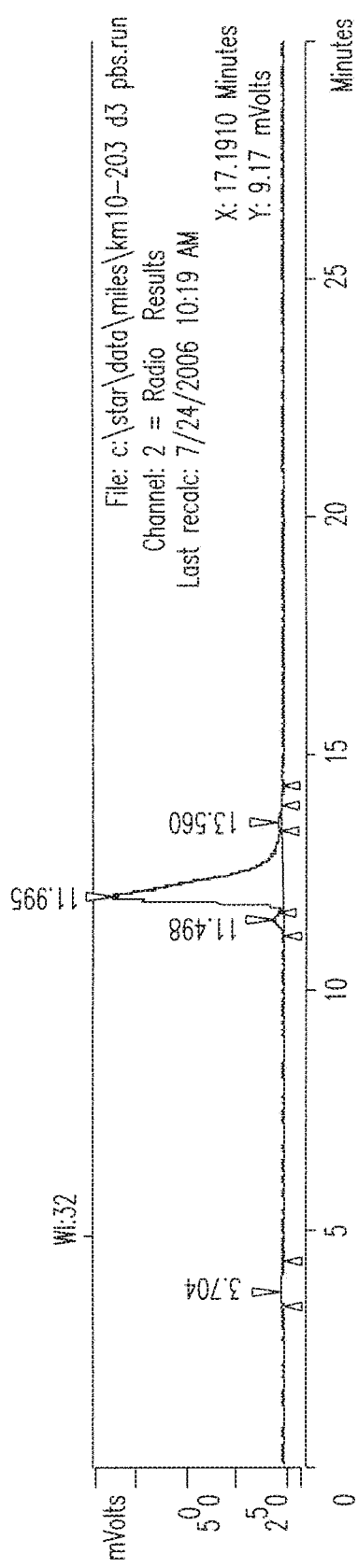
Figure 4D:
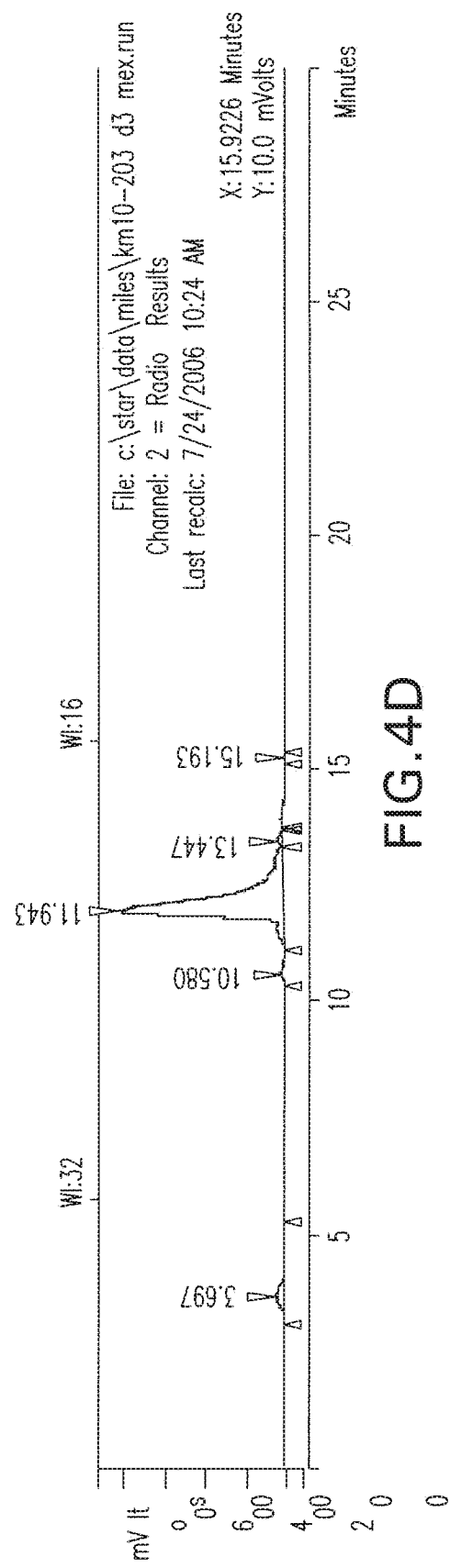

The stability of the radiolabeled compound in solution was determined as a function of time. Specifically, after radiolabeling and isolation, the product was stored at 37° C. for 3 days after which HPLC analysis was performed to check for degree of label retention, as well as potential product degradation. The reformation of NaI and the presence of the reduced iodates was analyzed. The results of the labeling stability study demonstrated no significant degradation of the I-131 1072 out to 3 days at room temperature in DMSO, 10% ethanol/saline, PBS pH 7.2 and 6% ascorbate/3% gentisic acid solution. The results of the study are shown in FIG. 4 Biological Characterization of SAAC-Urea-Glutamate Conjugates The newly prepared SAAC-urea-Glu conjugates were screened in a human prostate cancer cell binding assay using PSMA-positive, LnCap cells, and PSMA-negative, PC3 cells. Compounds demonstrating specific uptake or binding to PSMA-positive cells will be studied for tumor localization in vivo.

In vitro Cold Screening Assays Verses I-131 DCIT. LNCaP and PC3 human prostate cancer cells were obtained from American Type Culture Collection, Rockville, Md. LNCaP cells were maintained in RPMI-1640 medium supplemented with 10% fetal bovine serum (FBS). PC3 cells were grown in F12K medium supplemented with 10% FBS. Binding of the radiolabeled compound and competition with cold derivatives to LNCaP and PC-3 cells was performed according to the methods of Tang et al. (Tang, H,; Brown, M.; Ye, Y.; Huang, G.; Zhang, Y.; Wang, Y.; Zhai, H.; Chen, X.; Shen, T. Y.; Tenniswood, M., Prostate targeting ligands based on N-acetylated alpha-linked acidic dipeptidase, Biochem. Biophys. Res. Commun. 2003, 307, 8-14) with appropriate modifications. Cells were plated in 12-well plates at approximately 4×10$^5$ cells/well and incubated for 48 hours in a humidified incubator at 37° C./5% carbon dioxide prior to addition of compound. Each unique SAAC-urea-Glu conjugate was prepared and diluted in serum-free cell culture medium containing 0.5% bovine serum albumin (BSA) in combination with 3nM I-131 DCIT (known inhibitor). Total binding was determined by incubating I-131 DCIT without test compound. Plates were incubated at room temperature for 1 hour. Cells were removed from the plates by gently pipeting and transferred to eppendorff tubes. Samples were microcentrifuged for 15 seconds at 10K×g. The medium was aspirated and the pellet was washed twice by dispersal in fresh assay medium followed by microcentrifugation. Cell binding of I-131 DCIT was determined by counting the cell pellet in an automated gamma counter. Nonspecific binding was determined as the counts associated with the cells after incubating with 2 uM nonradiolabeled compound or 2-phosphonomethyl-pentanedioic acid (PMPA). The control compounds are depicted below.

Control Compounds

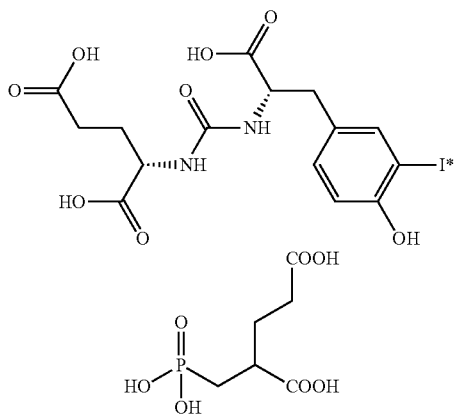

The two key compounds for the binding assays, are shown above: the I-DCIT (Kozikowski et al) and 2-Phosphonomethyl-pentanedioic acid (PMPA-right), a potent inhibitor with IC$_{50}$=6 nM.

Figure 5:
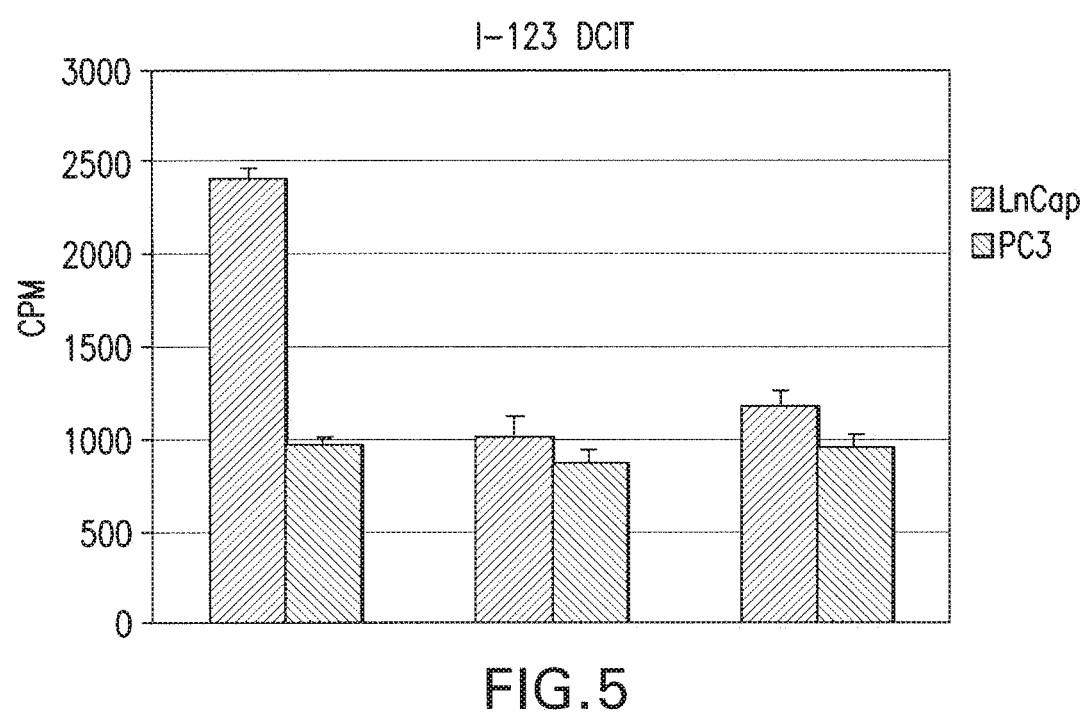
FIG. 5 shows I-123 DCIT bound specifically to LnCap cells and not PC3 cells (left set) as is evident by the counts displaceable by nonradiolabeled compound (middle set) or PMPA (right set) in LnCap cells. The histograms show the mean±SEM, each experiment was performed in duplicate.
Figure 6:
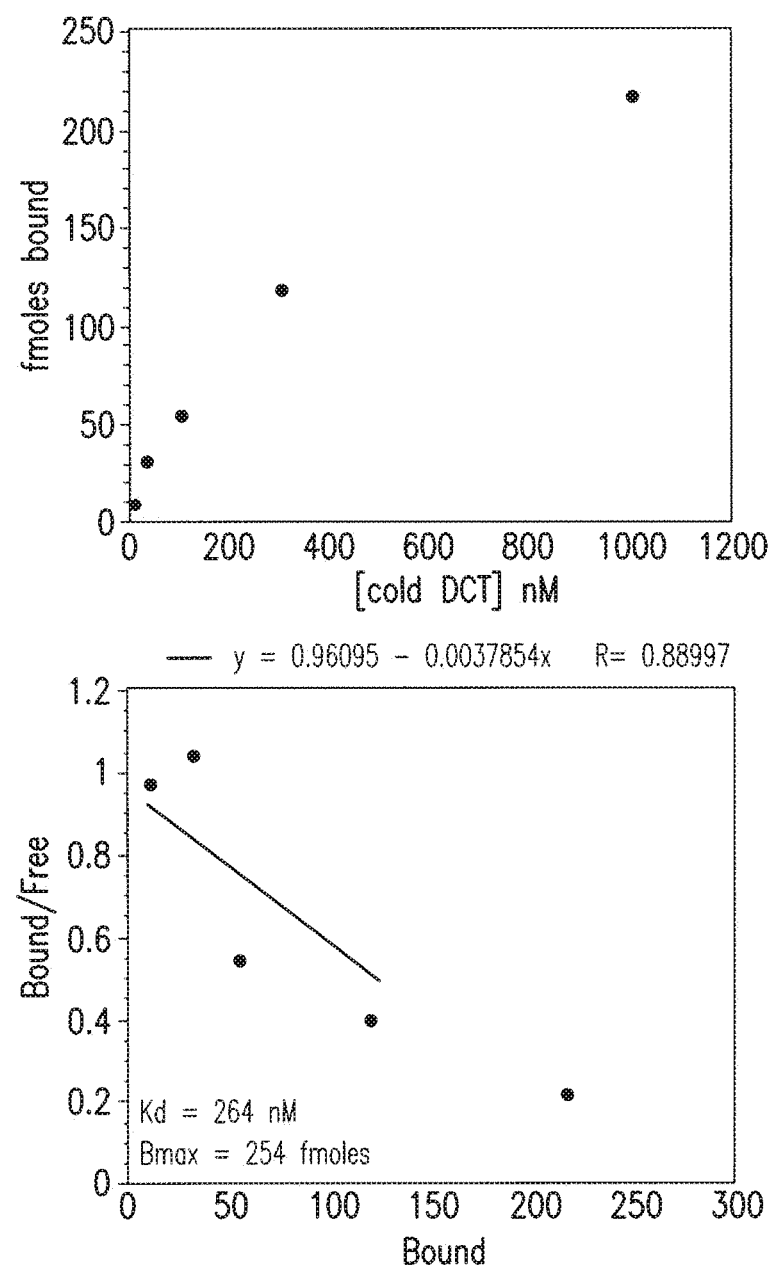
FIG. 6 is Scatchard Analysis in PSMA Cellular Binding Assay with cold 2-{3-[1-Carboxy-2-(4-hydroxy-phenyl)-ethyl]-ureido}-pentanedioic acid DCT).
Figure 7:
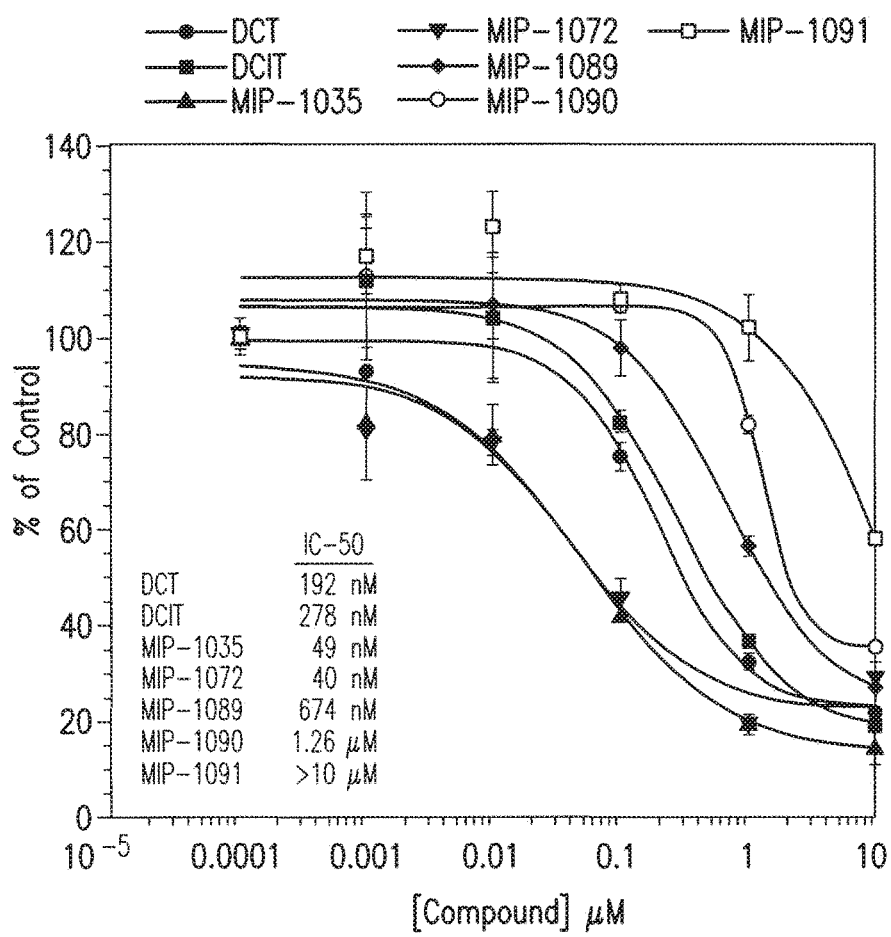
FIG. 7 shows biological assessments of selected compounds in the PSMA-positive LNCaP cells.
Figure 8:
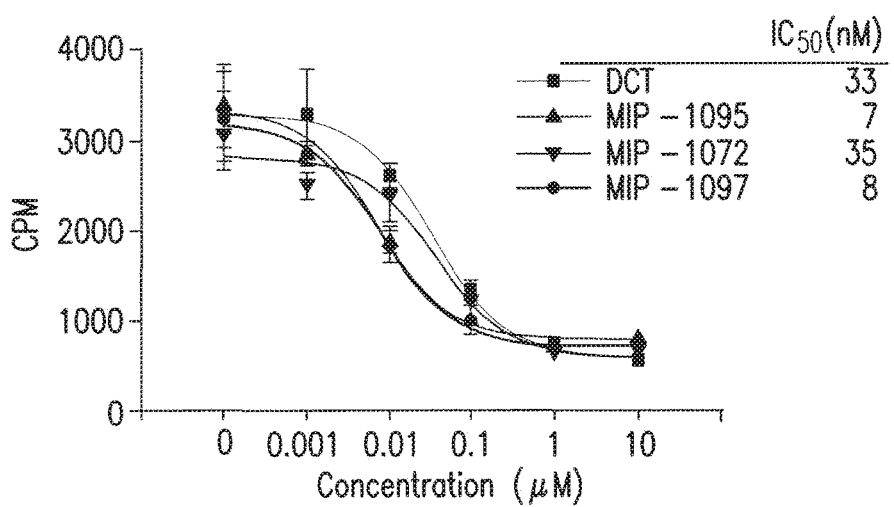
FIG. 8 show biological assessments of lead compounds in the PSMA-positive LNCaP cells.
Figure 9:
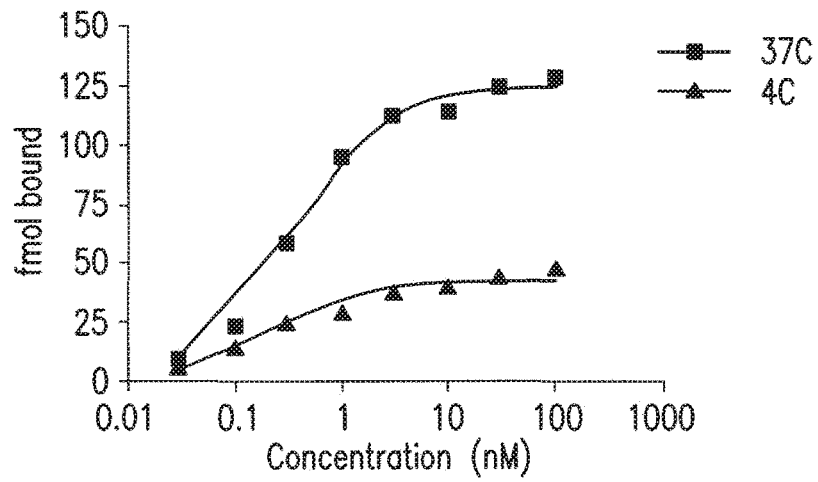
FIG. 9 Shows Scatchard Analysis in PSMA Cellular Binding Assay with MIP1072.

(ii) In vitro Dose Screening. I-131 DCIT bound specifically to LnCap cells and not PC3 cells as is evident by the counts displaceable by nonradiolabeled compound or PMPA in LnCap cells only (FIG. 5). Binding constants were determined by incubating LnCap cells with various amounts of nonradiolabeled DCIT in the presence of a constant amount of I-131 DCIT and dividing by the specific activity of each solution to determine the number of fmoles compound bound (FIG. 6). The Kd was determined to be 264 nM and Bmax was 254 fmoles. Compounds MIP-1008 and MIP-1033 which 2 uM competed with I-131 DCIT for binding to LnCap cells, were retested at various doses to determine IC-50 values (FIGS. 7 and 8). While MIP-1072, MIP-1095, and MIP-1097 displayed IC50 values <50 nm compounds MIP-1008 and MIP-1033 exhibited IC-50s of 98 nM and 497 nM, respectively. Compounds MIP-1025, MIP-1028, and MIP-1029 did not compete for binding (Table 1).

Figure 10:
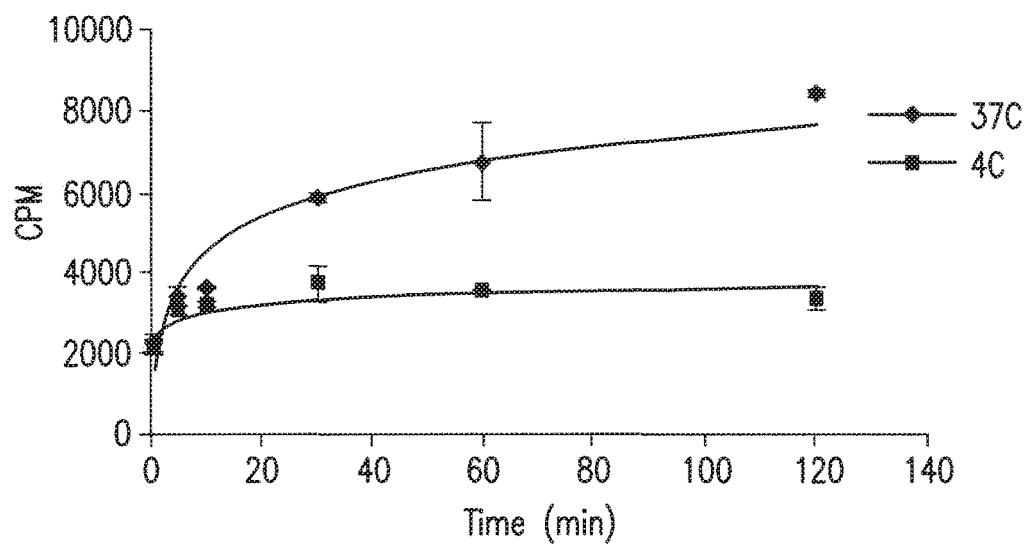
FIG. 10 shows internalization of I-131-MIP1072.

In order to confirm the results of the Scatchard analysis of FIG. 7 indicating MIP-1072 internalization into LNCaP cells, the rate of uptake of MIP-1072 in LNCaP cells was monitored. Each will was dosed with 100 nM MIP-1072 (2 uCi/well) at 4° C. and 37° C. Binding to PSMA reached equilibrium after 15 min as evidenced by the plateau in the curve at 4° C. The cell incubated at 37° C. continued to internalize MIP-1072 after equilibrium had been reached. This result, FIG. 10, confirms the Scatchard and indicates that MIP-1072 is indeed internalized.

(iii) Microsome Assay Experimental

Figure 11A:
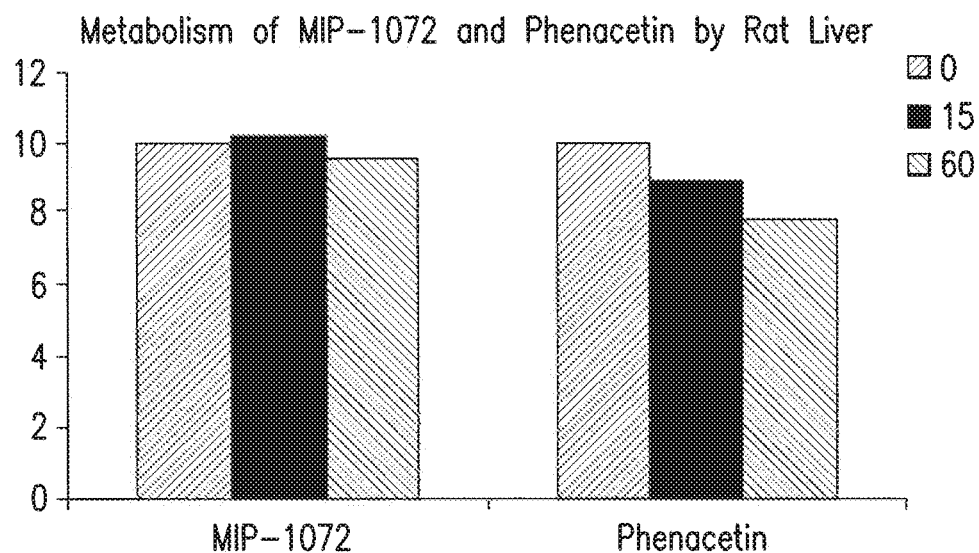
FIG. 11A and 11B respectively show stability of I-131 MIP-1072 verses DCT and Phenacetin in rat microsomes for 60 minutes.
Figure 11B:
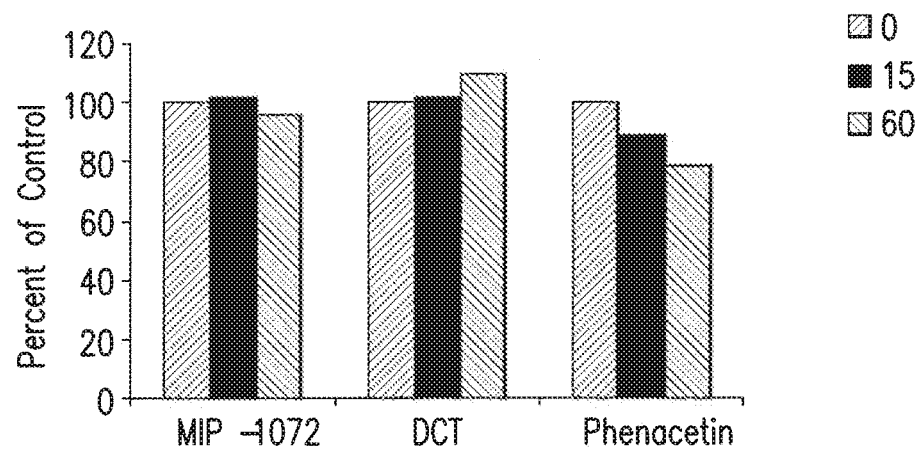

Pooled male rat liver microsomes (1 mg/mL, BD Biosciences), NADPH regenerating system (1.3 mM NADP, 3.3 mM glucose 6-phosphate and 0.4 U/mL glucose 6-phosphate dehydrogenase, BD Biosciences) and test compound (50 μM MIP-1072, 50 μM DCT, and 100 μM phenacetin) were added to 0.1 M potassium phosphate buffer (pH 7.4) in order to monitor the catastrophic degradation of the test compounds. The mixture was incubated at 37° C. and at the indicated time (0, 15, 60 min) the reaction was stopped by the addition of an equal volume of ice cold methanol (500 μL). The resulting slurry was then centrifuged at 21,000×G for 10 min and the supernatant was collected and injected onto an Agilent LCMS model MSD SL using a 95:5 water:acetonitrile (with 0.1% formic acid) to 40:60 water:acetonitrile (with 0.1% formic acid) gradient and monitoring for the parent ion only in single ion mode. The results, shown in FIGS. 11A and 11B, are expressed as degradation of the parent ion with respect to the 0 min time point.

The stability of MIP-1072 was assessed using rat liver microsomes. MIP-1072 (50 μM) and Phenacetin (100 μM) were incubated with rat liver microsomes at 37° C. for the indicated time. Phenacetin was used as a control substance that is known to be metabolized. MIP-1072 was not degraded by the rat live microsomes during the incubation period. However, phenacetin was degraded by 22% after a 60 min incubation.

The lead compound, MIP 1072, was I-131-labeled for tissue distribution studies in mice with both LNCaP (PSMA positive) and PC3 (PSMA negative) tumors implanted. The compound was radiolabeled by the route shown below.

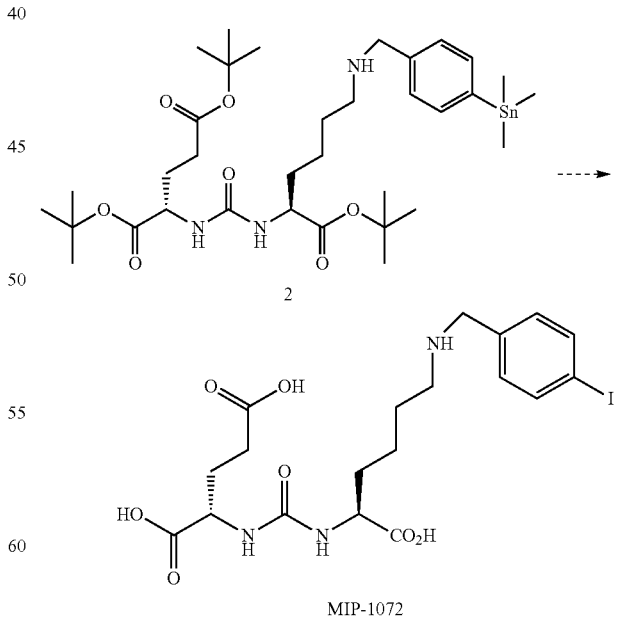

Figure 12:
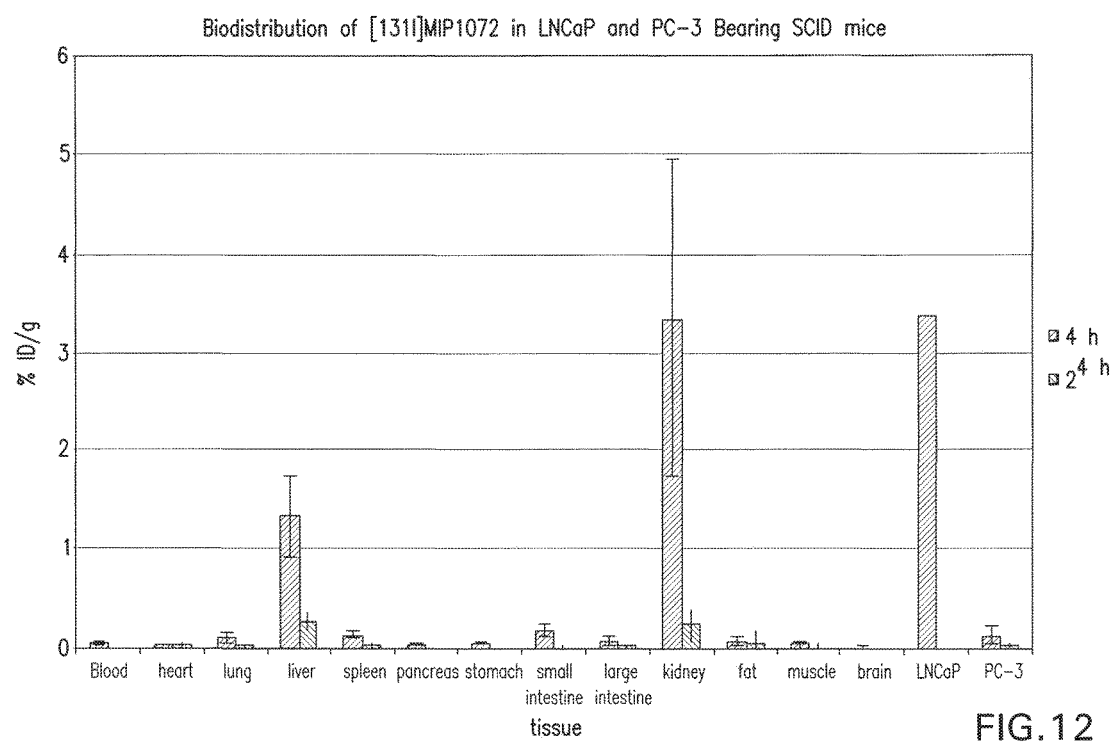
FIG. 12 shows tissue biodistribution of the I-131 MIP1072 in xenograft turmored mice.
Figure 13:
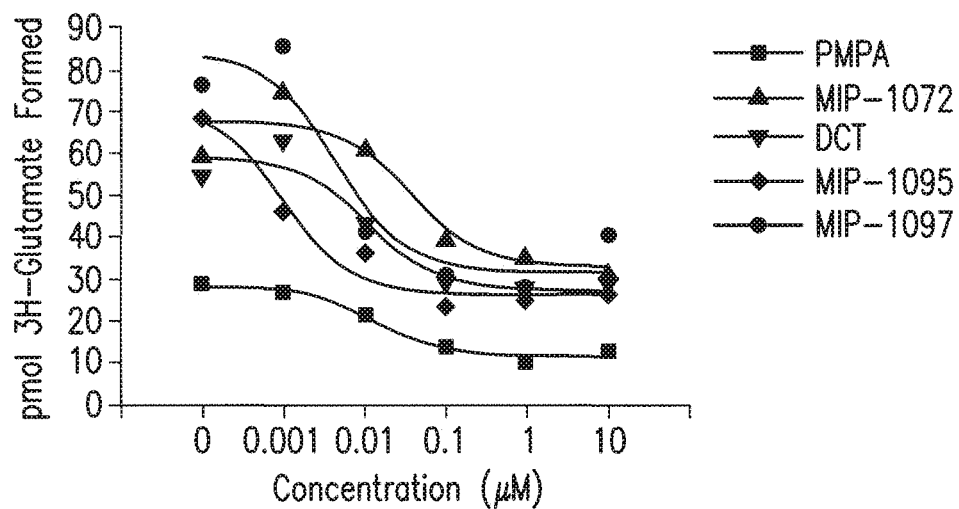
FIG. 13 shows inhibition of NAALADase activity from LNCaP cellular lysates.
Figure 14:
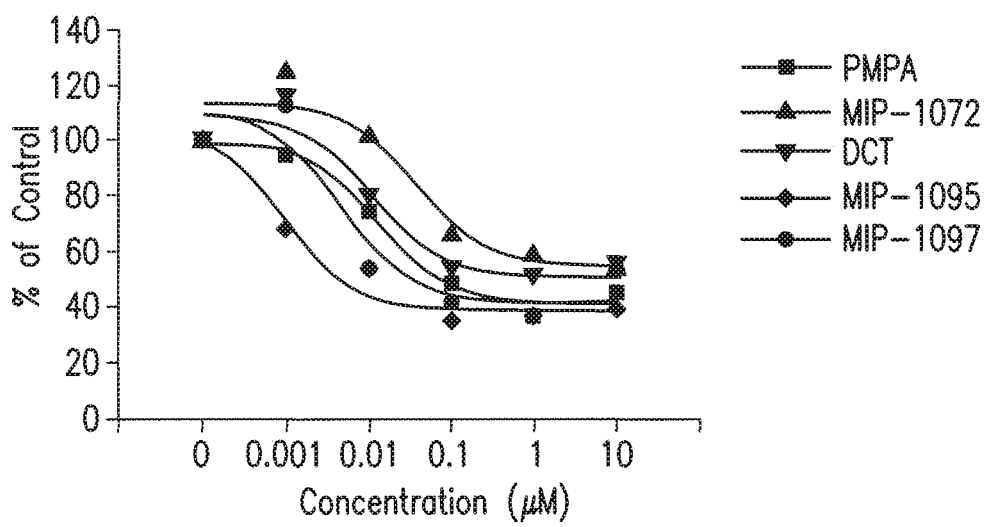
FIG. 14 shows inhibition of NAALADase Activity from LNCaP Cellular lysates.

The tissue biodistribution results, were consistent with the in-vitro data, and demonstrated significant uptake in the LNCaP (PSMA positive) tumors. The results also displayed a high degree of specificity with very little activity in the PC3 (PSMA negative) tumors. A graph depicting the mice distribution is shown below (FIG. 12).

The biological assessment using N-[N-[(S)-1,3-dicarboxypropyl]carbamoyl]-S-3-iodo-L-tyrosine (I-131-DCIT) verses "cold" complexes proved to be a rapid first screen, followed by dose curves to determine accurate $IC_{50}$ values. The lead series of compounds that exhibited IC50 values <50 nM. In vivo data of the lead series demonstrated high affinity, with 3% ID/g accumulating in the LNCaP tumors, and high specificity with the LNCaP-to-PC3 ratio exceeding 15-to 1.

LNCaP Cell Lysis Protocol
2 confluent T75 Flasks
Wash cells of the plate by pipetting up and down with media.
Wash with 0.32 M sucrose, re-centrifuge
Re-suspend cell pellet in 1 mL 50 mM Tris-HCl, pH 7.4, 0.5% Triton X-100
Centrifuge at 14000 rpm for 1 min to precipitate nuclei
Remove supernatant and divide into 50 uL aliquots
Store at −80 C
Protein Assay
Bio-Rad Protein Standard II—1.44 mg/ml
Since using detergent in lysis step, make working reagent, A' by adding 20 uL of reagent S to each 1 mL of reagent a that will be needed for the run. (If a precipitate forms, warm and vortex)
Prepare 5 protein dilutions—0, 0.2, 0.4, 0.8, 1.6 mg/mL
Also prepare 1/10, 1/100, and 1/1000 dilutions of the unknown
Combine 25 μL standard/unknown, 100 μL A', 800 μL reagent B in duplicate. Mix
After ~15 min measure absorbance at 750 nM
NAALADase Assay
Rxn Buffer: 50 mM Tris-HCl, pH 7.4, 20 mM CoCl2, 32 mM NaCl
Make cold NAAG (100 mM stock) dilute 1/100 in Rxn Buffer for 1 mM
Combine 600 uL buffer and LNCaP cell lysate (200 μg)
Pre-incubate 37 C for 3 min
Pre-incubate Rxn Buffer and LNCaP cell lysate for 3 min at 37 C
Add 8 μL of 1 mM NAAG (for 1 μM final conc) spiked with 1,000,000 CPM of $^3$H-NAAG (100 μL of 1 mM NAAG+ 10 μL of 3H-NAAG (10 μCi)). For competition add PMPA.
Incubate for 30 min
at indicated time, stop reaction by removing 100 uL of the reaction-mix and adding an equal volume of ice cold 0.25 M $KH_2PO_4$, pH 4.3 to stop the rxn
Apply ½ of mixture to 250 mg AG 50W-X4 cation exchange column (200-400 mesh, H⁺ form, swell resin with DI H2O prior to use). Save the other ½ for counting.
Wash column with 500 μL 1:1 Rxn Buffer/0.25M$KH_2PO_4$
Elute with 3M KCl (1.5 mL)
Count 100 uL of the load, elution and reaction (diluted 1.6) to minimize quenching
Notes
Time=0 control values will be subtracted from experimental time points
Results expressed as pmol $^3$H-glutamate formed/min/mg protein
Grant says inc only 10 min to ensure linearity, although Luthi-Carter, et al (J Pharm Exp Therap 1998 286(2)) says 2 hours still no effect on linearity and less than 20% of the substrate consumed Therapeutic Treatments Compounds of the present can be used to inhibit NAALADase for therapeutic treatments. Diseases that could be receptive to NAALADase treatment include painful and sensory diabetic neuropathy, neuronal damage and prostate cancer, schizophrenia, colorectal cancer, inflammation, amyotrophic lateral schlerosis, or diabetic neuropathy. The present compounds can also be used an analgesic. Guidance for the modeling of such therapeutic treatments can be found in Goodman & Gilman's The Pharmacological Basis of Therapeutics, McGraw Hill, 10 edition 2001, Pharmaceutical Preformulation and Formulation: A Practical Guid from Candidate Drug Selection to Commercial Dosage Form, CRC, 2001 and Handbook of Pharmaceutical Excipients, AphA Publications, 5 edition, 2005.

Figures 15, 16:
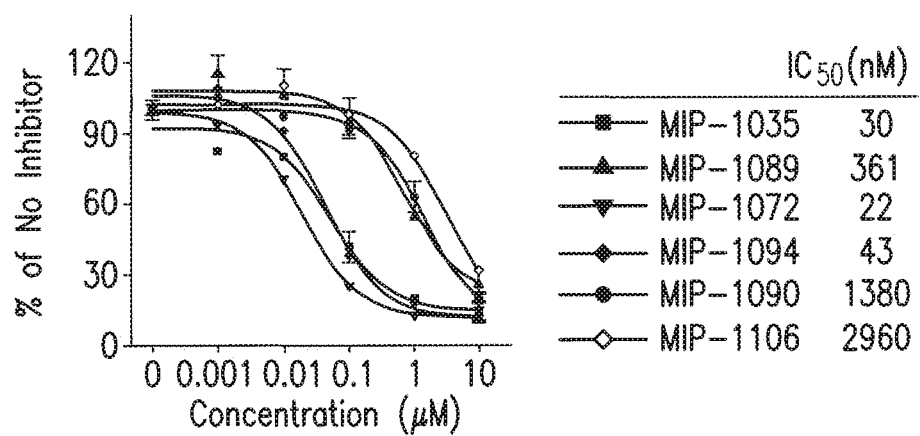
FIG. 15 shows inhibition of NAALADase Activity from LNCaP Cellular lysates.
FIG. 16 shows the ability of test compounds to inhibit the binding of a known NAALADase inhibitor, 131I-DCIT, to PSMA on LNCaP cells was examined. Cells were incubated with various concentrations of test compounds and 131I-DCIT for 1 hour then washed and counted to determine IC50 values.

Competitive Binding of Analogs (FIG. 16)

The ability of non-radioactive analogs to compete with $^{131}$I-DCIT for binding to PSMA was tested in the PSMA positive human prostate cancer cell line, LNCaP cells. LNCaP cells (300,000 cells/well) were incubated for 1 hour with 3 nM [$^{131}$I]-DCIT in the presence of 1-10,000 nM MIP-1072 in RPMI-1640 medium supplemented with 0.5% bovine serum albumin, then washed and counted in a gamma counter. All documents cited in this specification including paten applications are incorporated by reference in their entirety.

Direct Binding and Internalization of MIP-1072

Figure 17:
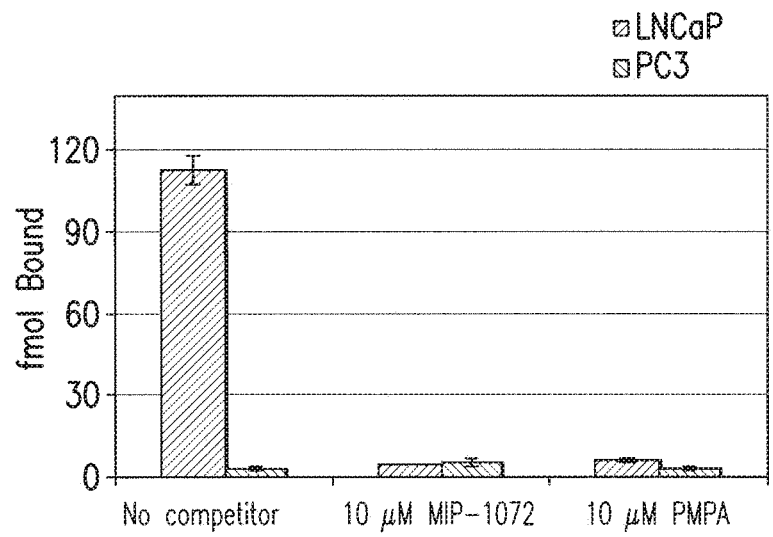
FIG. 17 is direct binding analysis of MIP-1072. $^{123}$I-MIP-1072 (3 nM, >1,000 mCi/µmole) was incubated with PSMA positive LNCaP cells or PSMA negative PC3 cells (300,000 cells/well), in both the absence and presence of either non-radioactive 10 µM MIP-1072 or 10 µM of a specific PSMA inhibitor (PMPA).

The direct binding of $^{123}$I-MIP-1072 to prostate cancer cells was examined (FIG. 17). LNCaP cells, or the PSMA negative cell line, PC3 cells, were incubated in RPMI-1640 medium supplemented with 0.5% bovine serum albumin for 1 hour with 3 nM $^{123}$I-MIP-1072 alone, or in the presence of 10 μM unlabeled MIP-1072, or 10 μM 2-(phosphonomethyl)-pentanedioic acid (PMPA), a structurally unrelated NAALADase inhibitor. Cells were washed and counted in a gamma counter.

Figure 18:
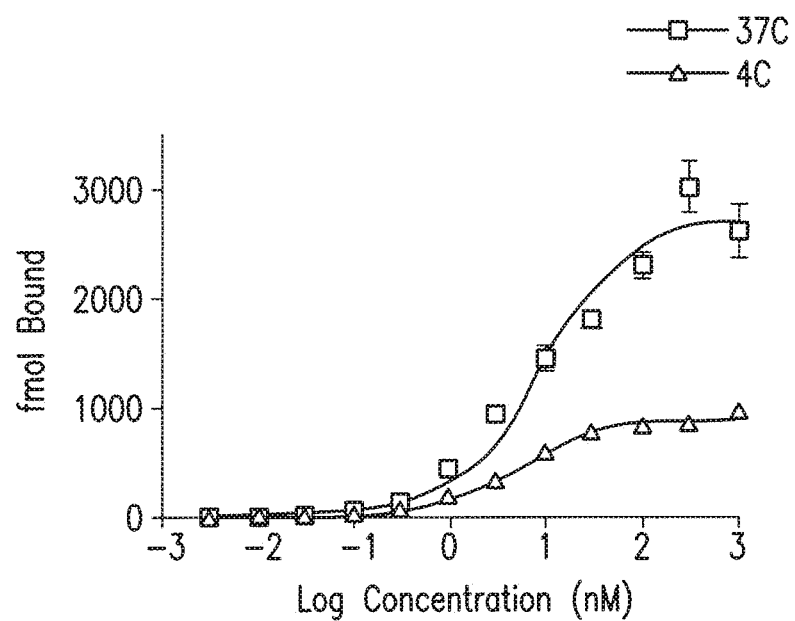
FIG. 18 shows saturation binding analysis of $^{123}$I-MIP-1072 in LNCaP cells.

The affinity constant ($K_d$) of MIP-1072 was determined by saturation binding analysis (FIG. 18). LNCaP cells were incubated for 1 hour with 30-100,000 pM $^{131}$I-MIP-1072 in HBS (50 mM Hepes, pH 7.5, 0.9% sodium chloride) at either 4° C. or 37° C. in the absence or presence of 10 μM unlabeled MIP-1072 (to determine non-specific binding). Cells were then washed and the amount of radioactivity was measured on a gamma counter. Specific binding was calculated as the difference between total binding and nonspecific binding. The affinity constant ($K_d$) of the interaction of MIP-1072 with PSMA on LNCaP cells was determined by saturation binding analysis performed by titrating $^{123}$I-MIP-1072 (3 pM-1,000 nM) in the presence and absence of an excess of non-radiolabeled MIP-1072 (10 μM). A $K_d$ of 4.8 nM, and Bmax of 1,490 fmoles/$10^6$ cells at 4° C. was determined by nonlinear regression analysis using Graph Pad Prism software (FIG. 18). The $K_d$ was not significantly different at 37° C. 8.1 nM. The Bmax, however, was greater at 37° C. than at 4° C.; 1,490 vs. 4,400 fmol/$10^6$ cells, respectively, indicating internalization of MIP-1072. The results below are representative of two independent analyses.

Figure 19:
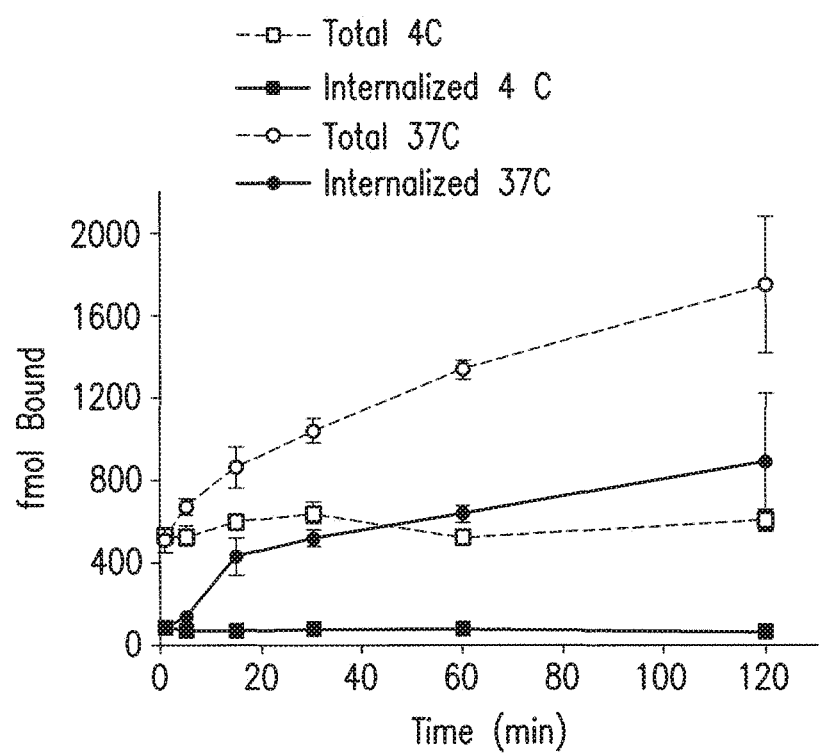
FIG. 19 shows internalization of $^{123}$I-MIP-1072.

The ability of MIP-1072 to internalize in LNCaP cells was confirmed by an acid wash assay (FIG. 19). LNCaP cells were incubated in HBS with 100 nM $^{123}$I-MIP-1072 for 0-2 hours at 4 and 37° C. At the indicated time the media was removed and the cells were incubated in mild acid buffer (50 mM glycine, 150 mM NaCl, pH 3.0) at 4° C. for 5 minutes. After the brief incubation the cells were centrifuged at 20,000×g for 5 minutes. The supernatant and cell pellet were counted in a gamma counter. In order to confirm the results of the saturation binding analysis indicating MIP-1072 internalization into LNCaP cells, we monitored the rate of uptake of MIP-1072 in LNCaP cells. Each well was dosed with 100 nM MIP-1072 (2 uCi/well) at 4° C. and 37° C. Binding to PSMA reached equilibrium after 15 min as evidenced by the plateau in the curve at 4° C. The cells incubated at 37° C. continued to internalize MIP-1072 after equilibrium had been reached. The results show a time dependent, acid insensitive increase in radioactivity associated with the pellet at 37° C. but not at 4° C., indicating that $^{123}$I-MIP-1072 is internalized at 37° C. but not at 4° C. (FIG. 19).

Tumor Uptake and Tissue Distribution of $^{123}$I-MIP-1072

Figure 20:
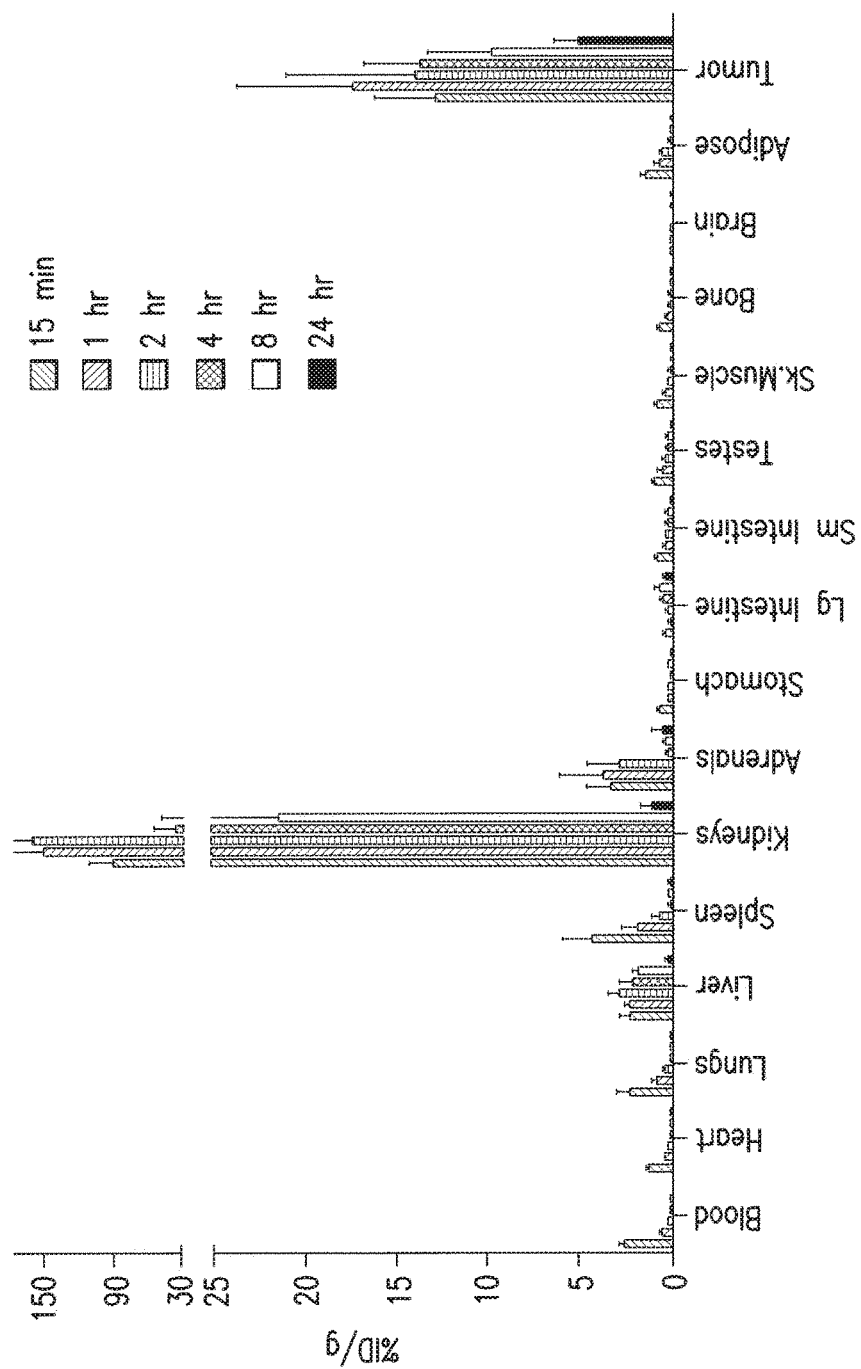
FIG. 20 shows uptake of $^{123}$I-MIP-1072 in LNCaP xenograft bearing mice. Tissue biodistribution of $^{123}$I-MIP-1072 (2 µCi/mouse, >1,000 mCi/µmole) was assessed in selected tissues from LNCaP (PSMA positive) tumor bearing nude mice. Results are expressed as the percent of the injected dose per gram of the selected tissues (% ID/g).
Figure 21:
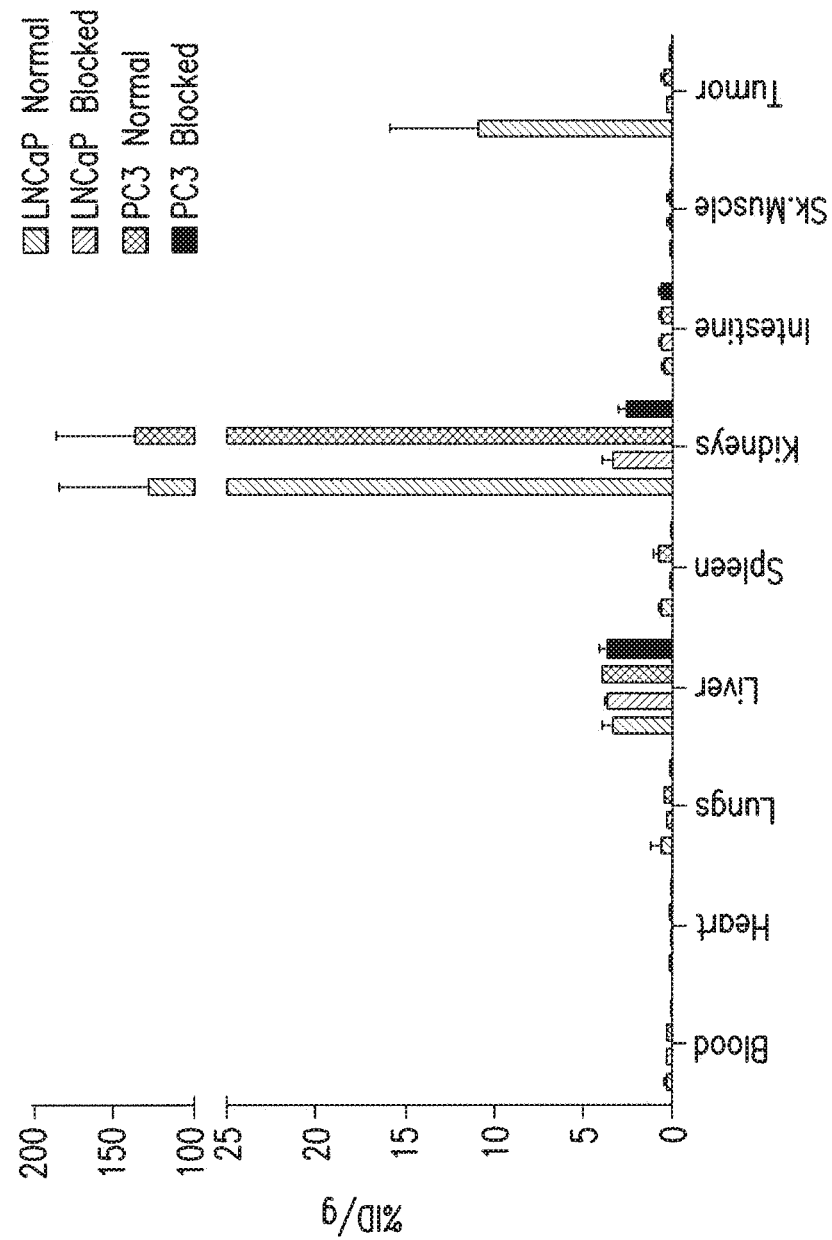
FIG. 21 Uptake of $^{123}$I-MIP-1072 in LNCaP and PC3 xenograft bearing mice. Tissue biodistribution of $^{123}$I-MIP-1072 (2 µCi/mouse, >1,000 mCi/µmole) was assessed in selected tissues from LNCaP (PSMA positive) and PC3 (PSMA negative) tumor bearing nude mice with (Blocked) or without (Normal) pretreatment with 50 mg/kg PMPA.

A quantitative analysis of the tissue distribution of $^{123}$I-MIP-1072 was performed in separate groups of make NCr Nude $^{-/-}$ mice bearing PSMA positive LNCaP xenografts (approximately 100-200 mm$^3$) administered via the tail vein as a bolus injection (approximately 2 μCi/mouse) in a constant volume of 0.05 ml. The animals (n=5/time point) were euthanized by asphyxiation with carbon dioxide at 0.25, 1, 2, 4, 8, and 24 hours post injection. Tissues (blood, heart, lungs, liver, spleen, kidneys, adrenals, stomach, large and small intestines (with contents) testes, skeletal muscle, bone, brain, adipose, and tumor) were dissected, excised, weighed wet, transferred to plastic tubes and counted in an automated γ-counter (LKB Model 1282, Wallac Oy, Finland). To compare uptake of $^{123}$I-MIP-1072 in LNCaP versus PC3 tumors, and to demonstrate that the compound was on mechanism via competition with 2-(phosphonomethyl)-pentanedioic acid (PMPA), some mice bearing either LNCaP or PC3 xenografts were pretreated with 50 mg/kg PMPA 5 minutes prior to injection with $^{123}$I-MIP-1072 and selected tissues were harvested at 1 hour post injection. MIP-1072, uptake and exposure was greatest in the kidneys and LNCaP xenograft which express high levels of PSMA. Peak uptake in the kidney was 158±46% ID/g at 2 hours and the LNCaP xenograft was 17±6% ID/g at 1 hours (FIG. 20). Uptake in these target tissues was rapid, whereas the washout was slower in the LNCaP xenograft. $^{123}$I-MIP-1072 was demonstrated to be on mechanism in vivo as evidenced by the localization to PSMA expressing LNCaP tumors but not PC3 tumors which do not express PSMA (FIG. 21). In addition, both the tumor and kidneys were blocked by pretreating the mice with PMPA, a potent inhibitor of PSMA.

What is claimed is:

1. A compound having the formula:

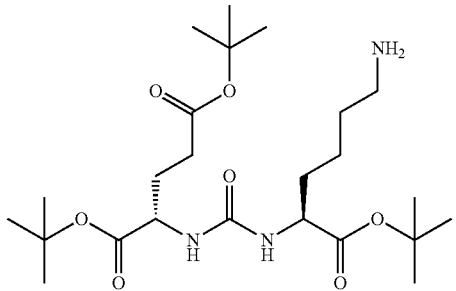

or a pharmaceutically acceptable salt thereof.

2. The compound of claim 1, wherein said pharmaceutically acceptable salt is selected from the group consisting of: a hydrochloric acid salt, a hydrobromic acid salt, a sulfuric acid salt, a nitric acid salt, a phosphoric acid salt, a methanesulfonic acid salt, a ethanesulfonic acid salt, a p-toluenesulfonic acid salt, and a salicylic acid salt.

3. The compound of claim 2, wherein said pharmaceutically acceptable salt is a hydrochloric acid salt.

* * * * *